(12) United States Patent
Matsumoto et al.

(10) Patent No.: US 7,541,922 B2
(45) Date of Patent: Jun. 2, 2009

(54) OPERATION CONTROL METHOD OF TWO DIMENSIONAL DIFFUSIVE SIGNAL-TRANSMISSION DEVICES, SIGNAL COMMUNICATION APPARATUS, AND CLOTHING PROVIDED WITH ANTENNA FUNCTION

(75) Inventors: Mitsuhiro Matsumoto, Tokyo (JP); Eiichi Ito, Chiba-ken (JP); Koji Tsuda, Saitama-ken (JP)

(73) Assignee: Hoya Corporation, Tokyo (JP)

( * ) Notice: Subject to any disclaimer, the term of this patent is extended or adjusted under 35 U.S.C. 154(b) by 738 days.

(21) Appl. No.: 11/291,774

(22) Filed: Dec. 2, 2005

(65) Prior Publication Data
US 2006/0146739 A1 Jul. 6, 2006

(30) Foreign Application Priority Data
Dec. 3, 2004 (JP) ............................. 2004-351063

(51) Int. Cl.
G08B 1/08 (2006.01)
(52) U.S. Cl. .............. 340/539.3; 340/568.1; 340/568.2; 340/573.1
(58) Field of Classification Search .............. 340/539.3, 340/568.1, 568.2, 572.1, 571, 573.1, 825.36, 340/825.49
See application file for complete search history.

(56) References Cited

U.S. PATENT DOCUMENTS

| 5,714,234 | A | * | 2/1998 | Robertson | ................. 428/195.1 |
| 6,424,315 | B1 | * | 7/2002 | Glenn et al. | ................. 343/895 |
| 6,740,945 | B2 | * | 5/2004 | Lepert et al. | ................. 257/414 |
| 2002/0167500 | A1 | * | 11/2002 | Gelbman | ..................... 345/204 |
| 2002/0173718 | A1 | | 11/2002 | Frisch et al. | |
| 2003/0023150 | A1 | | 1/2003 | Yokoi et al. | |
| 2004/0252729 | A1 | | 12/2004 | Shinoda et al. | |
| 2005/0194012 | A1 | | 9/2005 | Ito et al. | |
| 2005/0195118 | A1 | | 9/2005 | Ito et al. | |
| 2005/0195785 | A1 | | 9/2005 | Matsumoto et al. | |
| 2007/0024551 | A1 | * | 2/2007 | Gelbman | ..................... 345/85 |

FOREIGN PATENT DOCUMENTS

| JP | 2001-046357 | 2/2001 |
| JP | 2003-019111 | 1/2003 |
| JP | 2003-038425 | 2/2003 |

(Continued)

OTHER PUBLICATIONS

U.S. Appl. No. 11/291,934 to Matsumoto et al., filed Dec. 2, 2005.

(Continued)

Primary Examiner—Daryl C Pope
(74) Attorney, Agent, or Firm—Greenblum & Bernstein P.L.C.

(57) ABSTRACT

An operation control method to be implemented by each of a plurality of communication devices two-dimensionally arranged on a two dimensional diffusive signal-transmission board, each of the plurality of communication devices being configured to communicate by transmitting a transmission signal carrying data to another of the plurality of the communication devices using a two dimensional diffusive signal-transmission technology, the method includes judging whether a communication device being operated in a normal mode satisfies a predetermined condition, and setting the communication device into one of a low electrical power consumption mode in which at least one function is decreased, and a power off mode in which electrical power supply to the communication device is shut off, when the communication device being operated in the normal mode satisfies the predetermined condition.

20 Claims, 25 Drawing Sheets

FOREIGN PATENT DOCUMENTS

| | | |
|---|---|---|
| JP | 2003-188882 | 7/2003 |
| JP | 2004-007449 | 1/2004 |

OTHER PUBLICATIONS

English language Abstract of JP 2003-188882 (Jul. 4, 2003).
English language Abstract of JP 2001-046357 (Feb. 20, 2001).
English language Abstract of JP 2003-019111 (Jan. 21, 2003).
English language Abstract of JP 2003-038425 (Feb. 12, 2003).
English language Abstract of JP 2004-007449 (Jan. 8, 2004).

\* cited by examiner

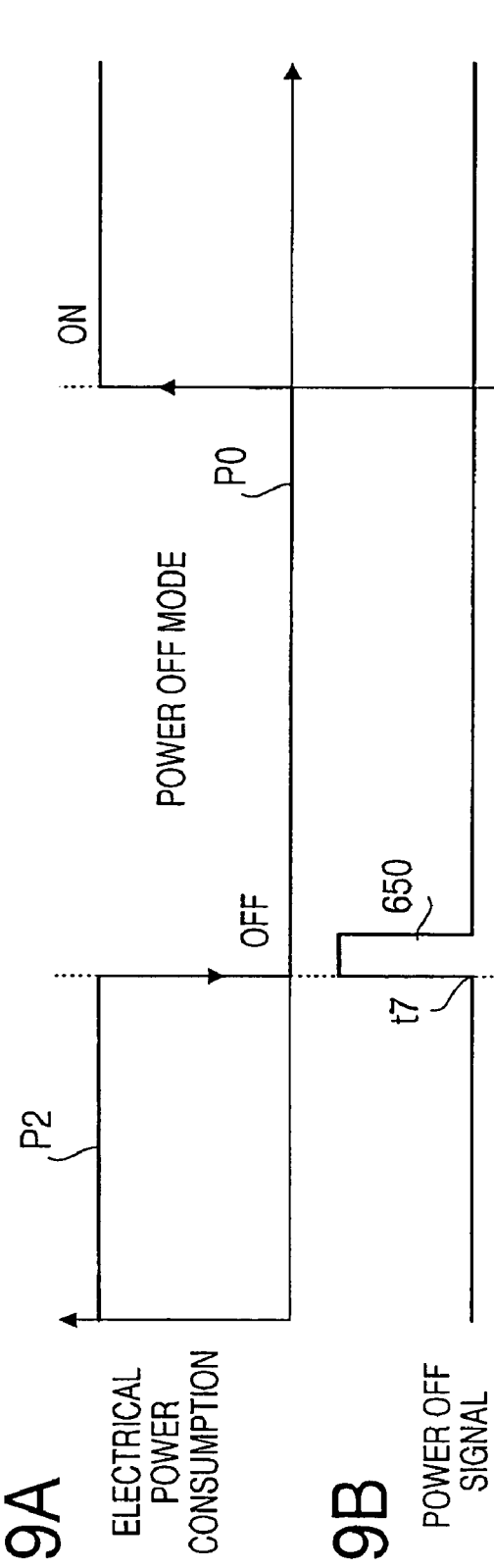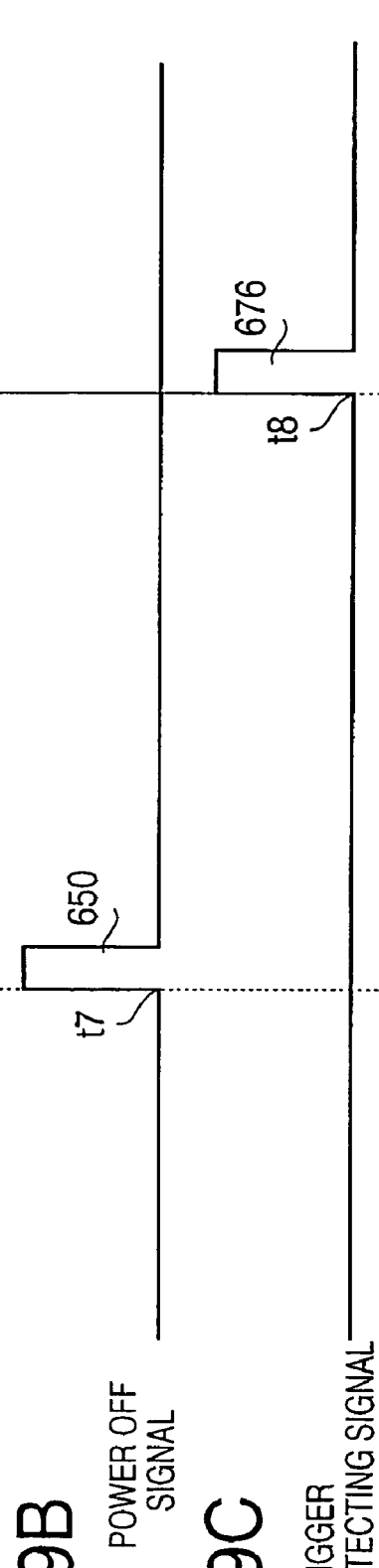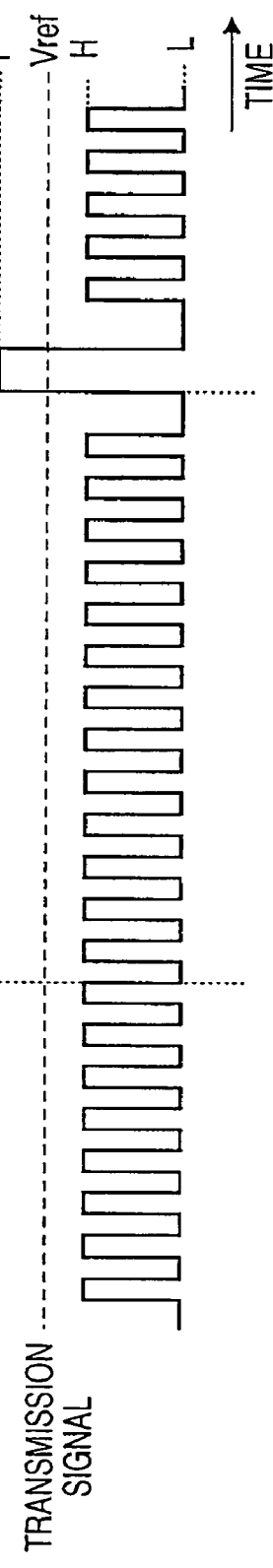
FIG.19A ELECTRICAL POWER CONSUMPTION
FIG.19B POWER OFF SIGNAL
FIG.19C TRIGGER DETECTING SIGNAL
FIG.19D TRANSMISSION SIGNAL

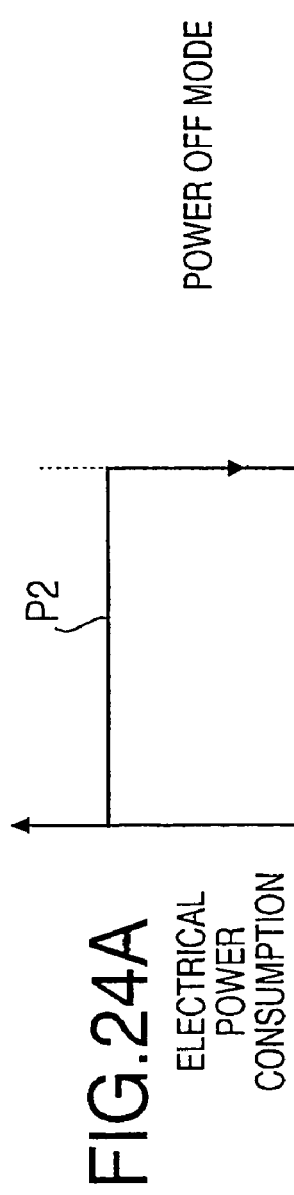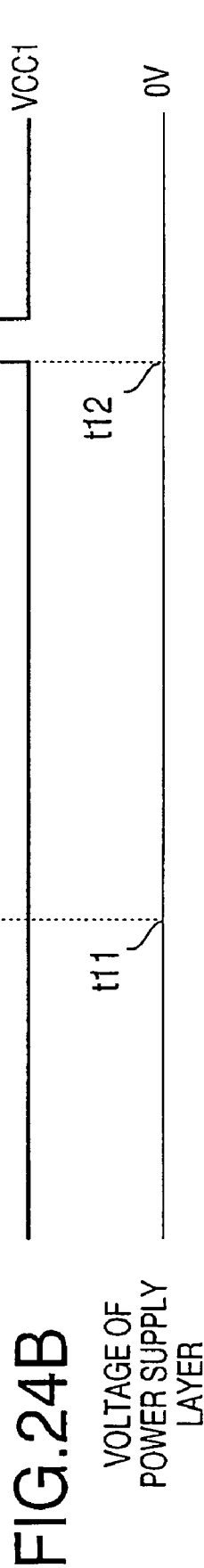

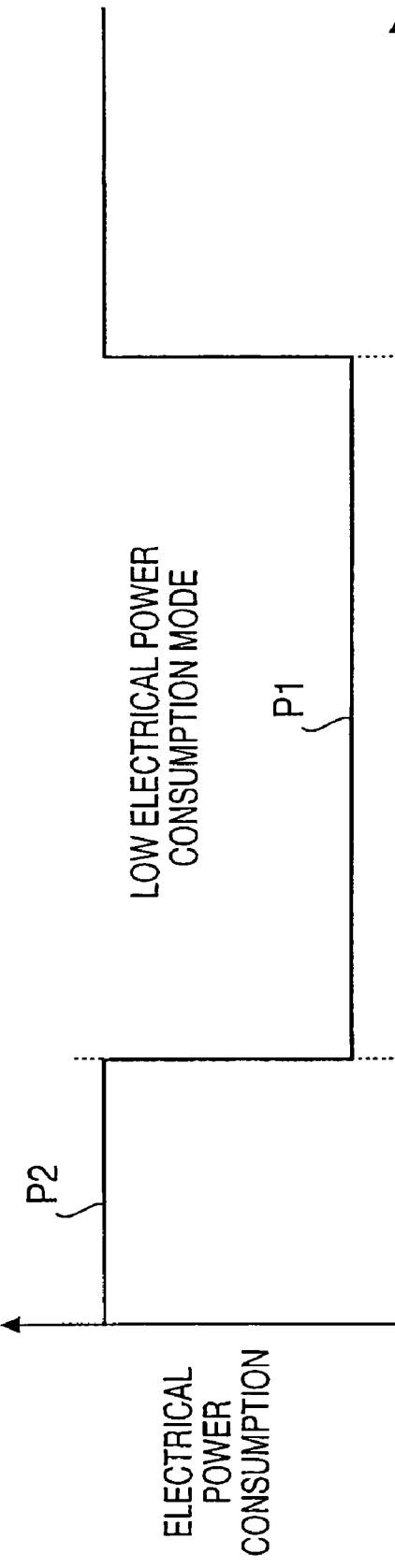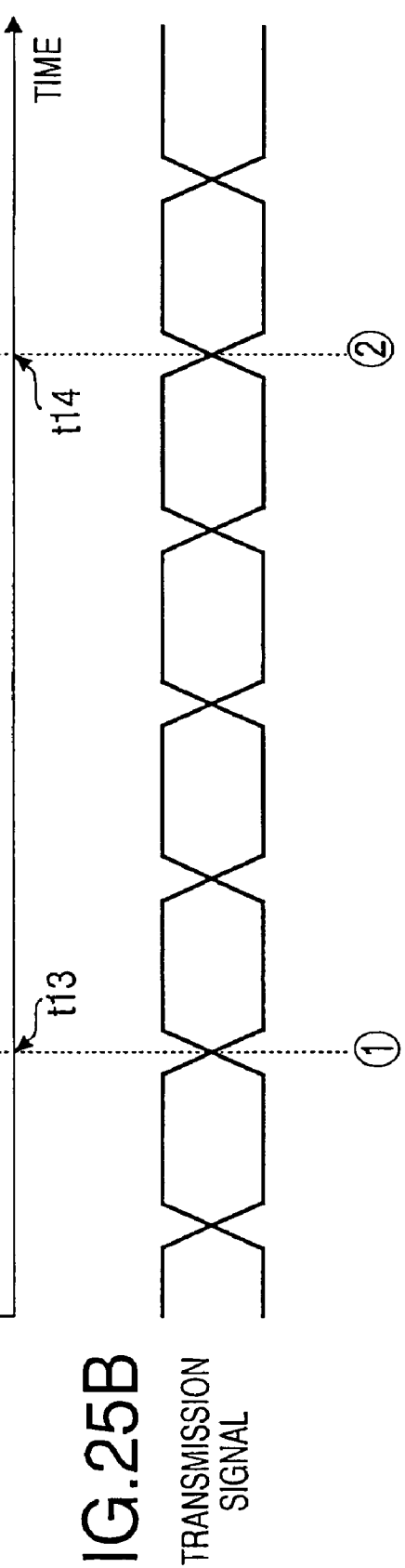

OPERATION CONTROL METHOD OF TWO DIMENSIONAL DIFFUSIVE SIGNAL-TRANSMISSION DEVICES, SIGNAL COMMUNICATION APPARATUS, AND CLOTHING PROVIDED WITH ANTENNA FUNCTION

BACKGROUND OF THE INVENTION

The present invention relates to a method of controlling operation of two dimensional diffusive signal-transmission devices which are capable of communicating with each other using a two dimensional diffusive signal-transmission technology. More particularly, the present invention relates to a signal communication apparatus and clothing, provided with an antenna function, which use the method of controlling operation of two dimensional diffusive signal-transmission devices.

Japanese Unexamined Patent Publication No. 2003-188882 discloses a two dimensional diffusive signal-transmission technology (hereinafter, simply referred to as a 2D-DST technology) for transmitting a signal with a plurality of communication devices (hereinafter, referred to as 2D-DST devices) serving as transmission sites, without forming patterned wiring.

Japanese Unexamined Patent Publication No. 2003-188882 proposes a signal communication apparatus including a plurality of 2D-DST devices scattered on two-dimensional plane therein. Each of the plurality of 2D-DST devices is configured to communicate only with adjacent 2D-DST devices thereto within a predetermined communication distance. By means of such a local communication, a signal is transmitted in sequence from one of the 2D-DST devices to another. This makes it possible to transmit a signal to an intended 2D-DST device. The plurality of 2D-DST devices are categorized into hierarchies based on their predetermined management functions. In each of the hierarchies, a transmission channel data is set such that a signal can be efficiently transmitted to a final destination.

However, according to Japanese Unexamined Patent Publication No. 2003-188882, it is only a part of all the 2D-DST devices that contributes to the signal transmission. Nonetheless, all the 2D-DST devices are always powered on, which causes extremely high electric power consumption of the whole apparatus.

SUMMARY OF THE INVENTION

The present invention is advantageous in that a method of controlling operation of 2D-DST devices is provided. The 2D-DST devices are employed in a signal communication apparatus using a 2D-DST technology. The method is capable of reducing electrical power consumption of the 2D-DST devices and/or the whole signal communication apparatus.

According to an aspect of the invention, there is provided an operation control method to be implemented by each of a plurality of communication devices two-dimensionally arranged on a two dimensional diffusive signal-transmission board, each of the plurality of communication devices being configured to communicate by transmitting a transmission signal carrying data to another of the plurality of communication devices using a two dimensional diffusive signal-transmission technology, the method including judging whether a communication device being operated in a normal mode satisfies a predetermined condition, and setting the communication device into one of a low electrical power consumption mode in which at least one function is decreased, and a power off mode in which electrical power supply to the communication device is shut off, when the communication device being operated in the normal mode satisfies the predetermined condition.

Optionally, the predetermined condition may include a condition where the communication device has not received the transmission signal for a predetermined time period.

Optionally, each of the plurality of communication devices may be given its own ID to identify itself. Further, the transmission signal may include the IDs of the communication devices that are to be on a transmission channel. In this case, the predetermined condition may include a condition where the communication device has not received the transmission signal including its own ID for a predetermined time period.

Optionally, the transmission signal may include a sleep command designating the IDs to be set into one of the low electrical power consumption mode and the power off mode. In this case, the predetermined condition may include a condition where the ID of the device corresponds to one of the IDs designated by the sleep command included in the transmission signal received by the device.

Alternatively or optionally, the predetermined condition may include at least one of a first condition where the communication device has not received the transmission signal for a predetermined time period, a second condition where the communication device has not received the transmission signal including its own ID for a predetermined time period, and a third condition where the ID of the device corresponds to one of the IDs designated by the sleep command included in the transmission signal received by the device.

Optionally, the communication device is set back into the normal mode, when it receives an external trigger while being operated in one of the low electrical power consumption mode and the power off mode.

According to another aspect of the invention, there is provided a signal communication apparatus, which includes a plurality of communication devices two-dimensionally arranged on a board, each of the plurality of communication devices being configured to communicate using a two dimensional diffusive signal-transmission technology, and a control unit configured to control the whole of the signal communication apparatus. The board includes a power supply layer configured to supply electrical power to each of the plurality of communication devices, a ground layer configured to ground each of the plurality of communication devices, a signal layer configured such that a transmission signal is transmitted among the plurality of communication devices, and a plurality of insulating layers configured to electrically isolate the power supply layer, the ground layer, and the signal layer from each other.

Optionally, each of the plurality of communication devices may include an antenna configured to receive a signal outputted from an external sensor.

Optionally, each of the plurality of communication devices may include a trigger detecting system configured to detect an external trigger.

Still optionally, the board may further include a trigger layer configured such that the trigger detecting system detects the external trigger transmitted therethrough.

Optionally, the trigger detecting system may be configured to detect the external trigger transmitted through one of the power supply layer and the signal layer.

Yet optionally, the trigger detecting system may include a switching system configured to select one of electrical connection and cutting between the power supply layer and the communication device.

Further, the trigger detecting system may include a comparing system configured to compare a signal including the external trigger with a reference signal.

Optionally, each of the plurality of communication devices may be configured to be set into one of a low electrical power consumption mode in which at least a part of functions thereof is brought down, and a power off mode in which electrical power supply thereto is shut off, when it satisfies a predetermined condition while being operated in a normal mode.

Optionally, the predetermined condition may include a condition where the communication device has not received the transmission signal for a predetermined time period.

Optionally, each of the plurality of communication devices may be given its own ID to identify itself. Optionally, the transmission signal may include the IDs of the communication devices that are to be on a transmission channel. In this case, the predetermined condition may include a condition where the communication device has not received the transmission signal including its own ID for a predetermined time period.

Optionally, the transmission signal may include a sleep command designating the IDs to be set into one of the low electrical power consumption mode and the power off mode. In this case, the predetermined condition may include a condition where the ID of the device corresponds to one of the IDs designated by the sleep command included in the transmission signal received by the device.

Alternatively or optionally, the predetermined condition may include at least one of a first condition where the communication device has not received the transmission signal for a predetermined time period, a second condition where the communication device has not received the transmission signal including its own ID for a predetermined time period, and a third condition where the ID of the device corresponds to one of the IDs designated by the sleep command included in the transmission signal received by the device.

Optionally, the communication device operated in one of the low electrical power consumption mode and the power off mode may be set back into the normal mode, when it receives an external trigger.

According to a further aspect of the invention, there is provided clothing provided with a signal communication apparatus, which includes a plurality of communication devices two-dimensionally arranged on a board, each of the plurality of communication devices being configured to communicate using a two dimensional diffusive signal-transmission technology, and a control unit configured to control the whole of the signal communication apparatus. The board includes a power supply layer configured to supply electrical power to each of the plurality of communication devices, a ground layer configured to ground each of the plurality of communication devices, a signal layer configured such that a transmission signal is transmitted among the plurality of communication devices, and a plurality of insulating layers configured to electrically isolate the power supply layer, the ground layer, and the signal layer from each other. Each of the plurality of communication devices includes an antenna configured to receive a signal outputted from an external sensor, and a trigger detecting system configured to detect an external trigger. Each of the plurality of communication devices is configured to be set into one of a low electrical power consumption mode in which at least one function is lowered, and a power off mode in which electrical power supply thereto is shut off, when it satisfies a predetermined condition while being operated in a normal mode. Each of the plurality of communication devices is configured to be set back into the normal mode, when it receives the external trigger while being operated in one of the low electrical power consumption mode and the power off mode.

BRIEF DESCRIPTION OF THE
ACCOMPANYING DRAWINGS

FIG. 1 schematically shows the configuration of an endoscope system according to the present invention;

FIG. 2 shows the configuration of a capsule endoscope according to the present invention;

FIG. 3 schematically shows a 2D-DST board applied to a jacket provided with an antenna function;

FIG. 4 schematically shows a basic cross-sectional structure of the 2D-DST board;

Figure 14:
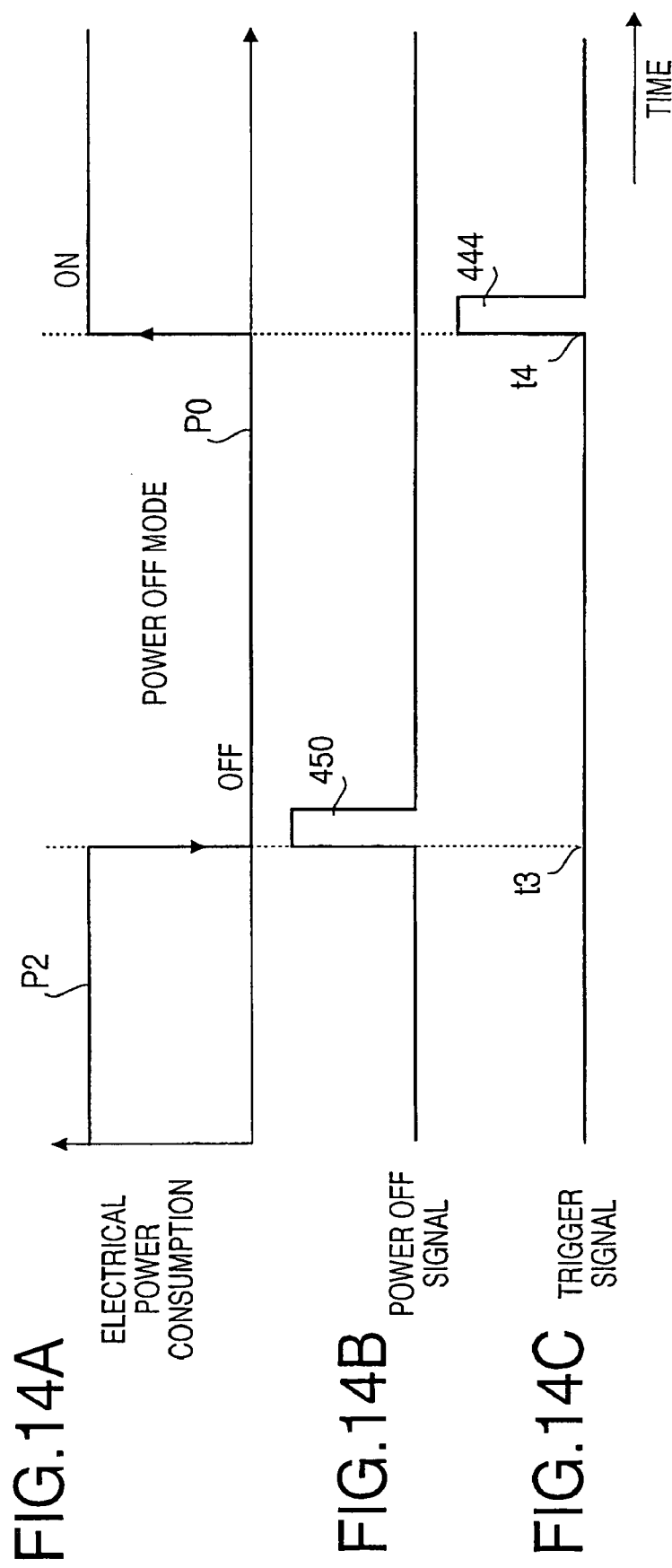
Figure 15:
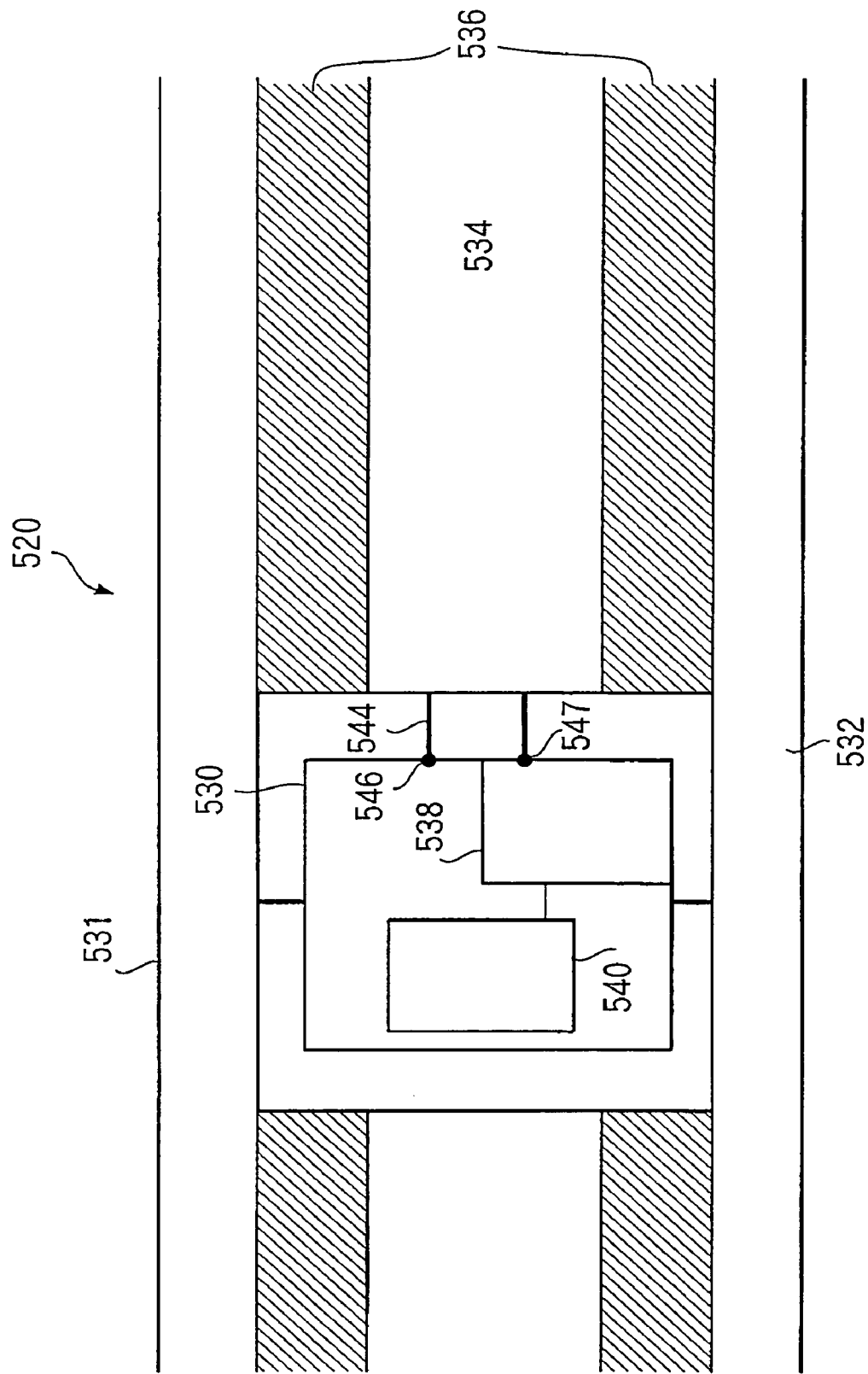
Figure 16:
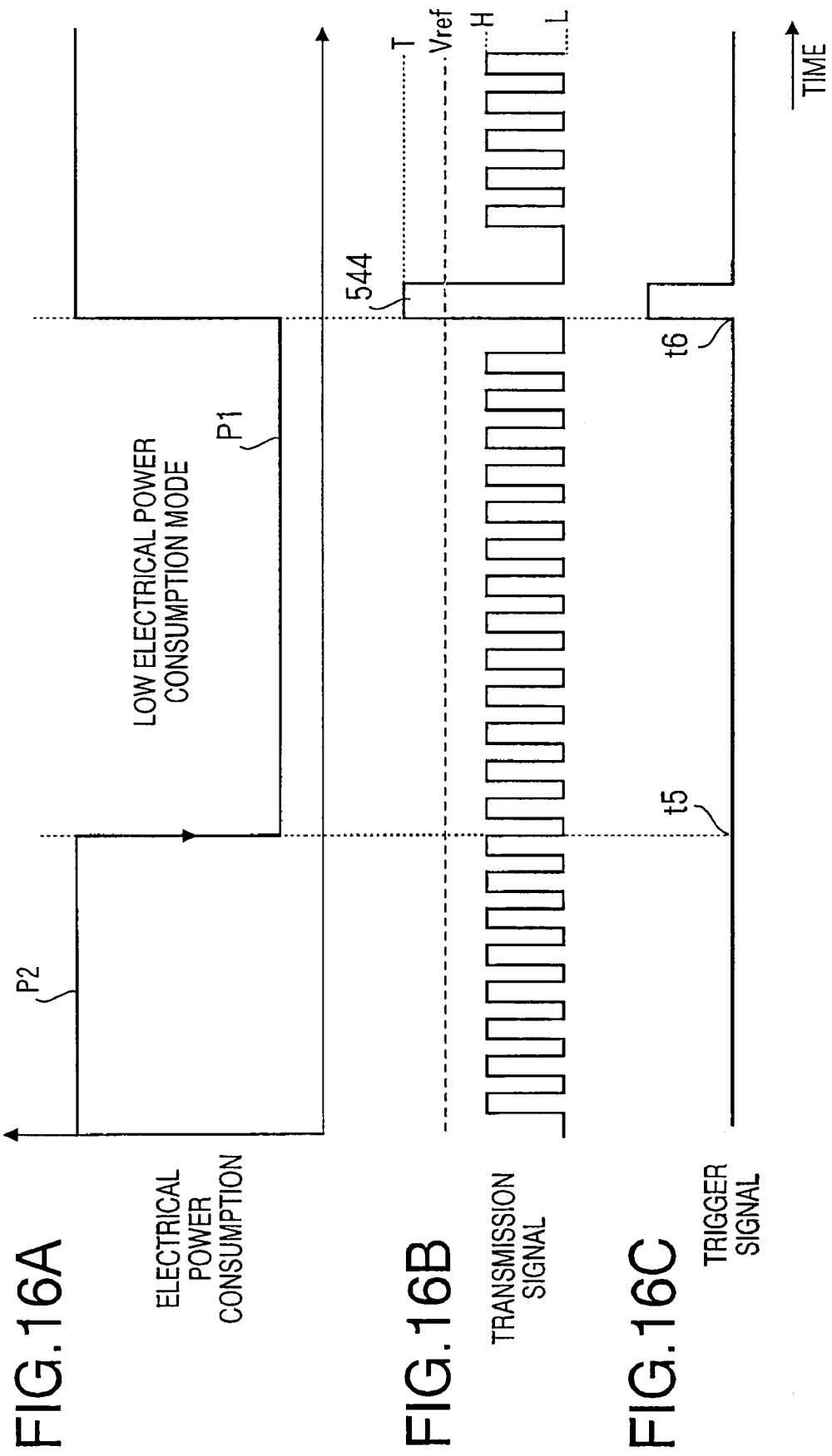
Figure 17:
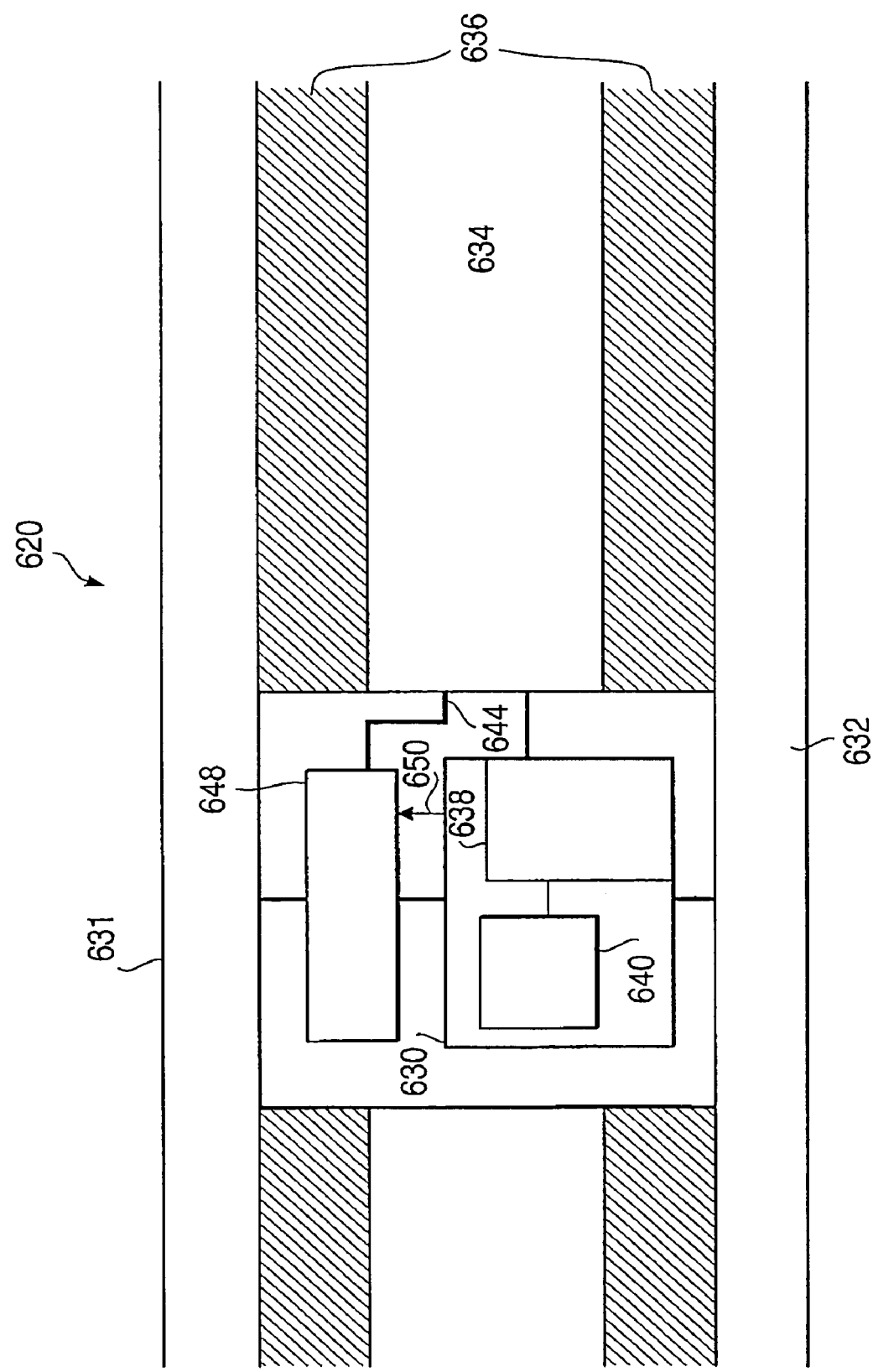
Figure 18:
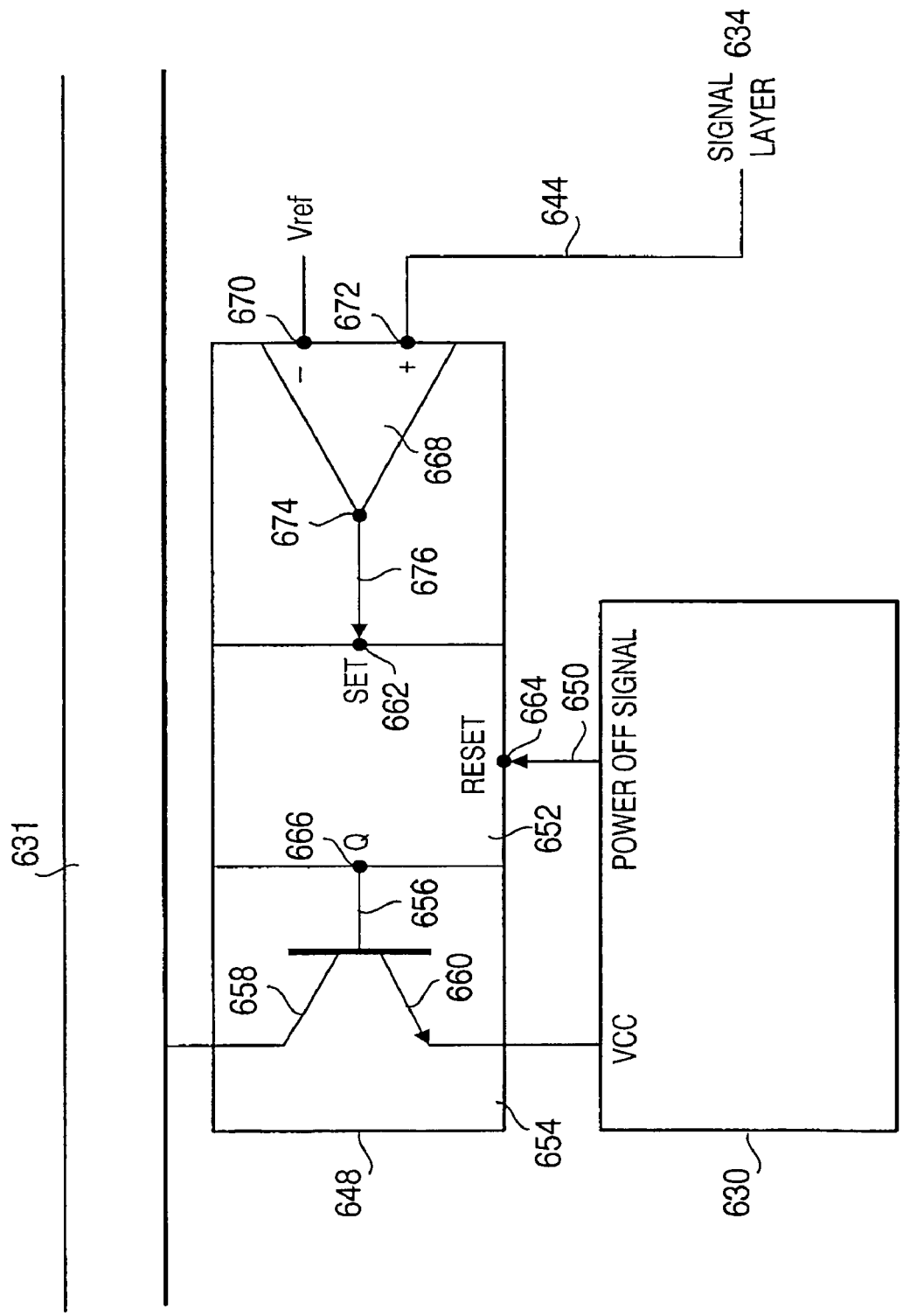
Figure 20:
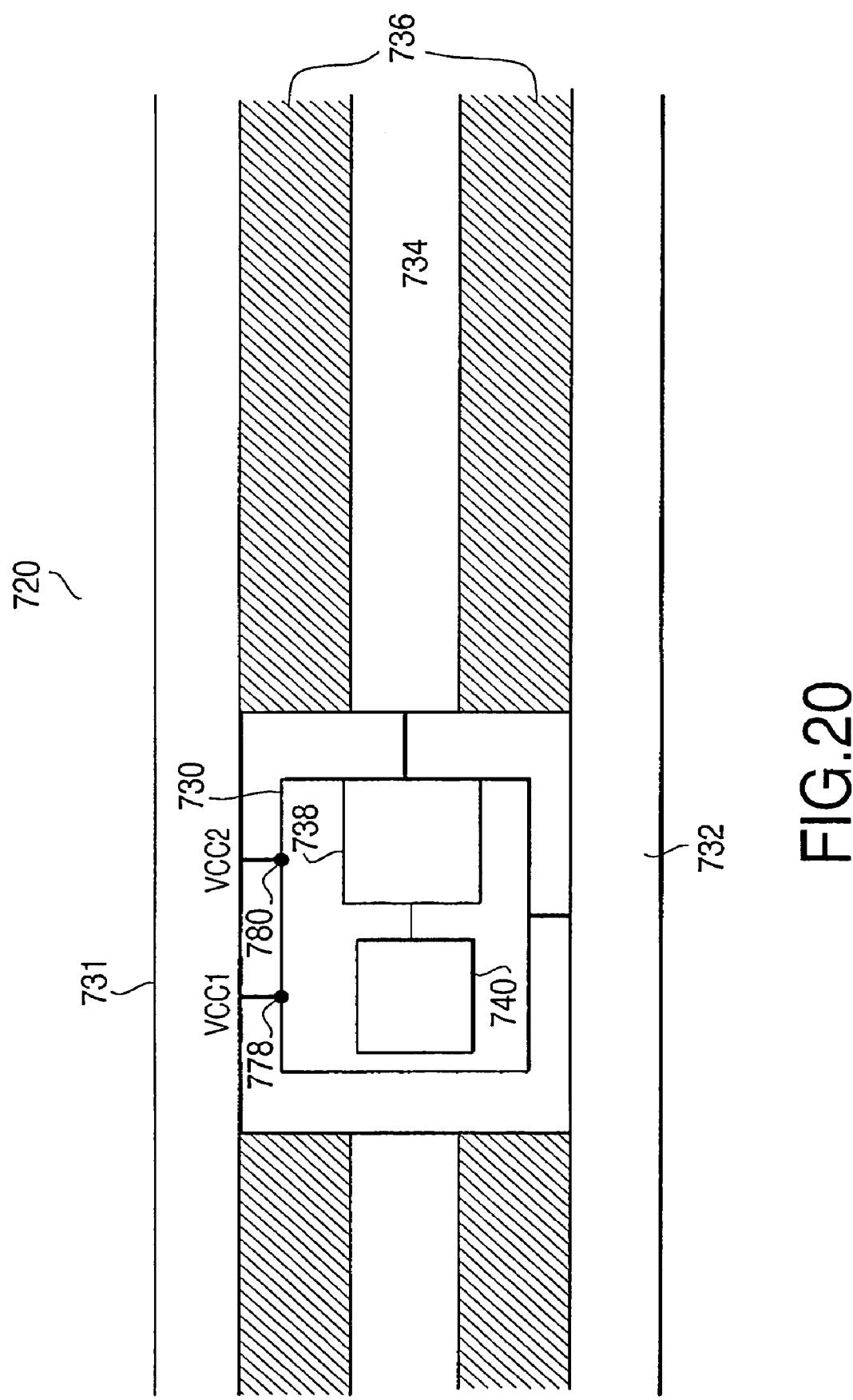
Figure 21:
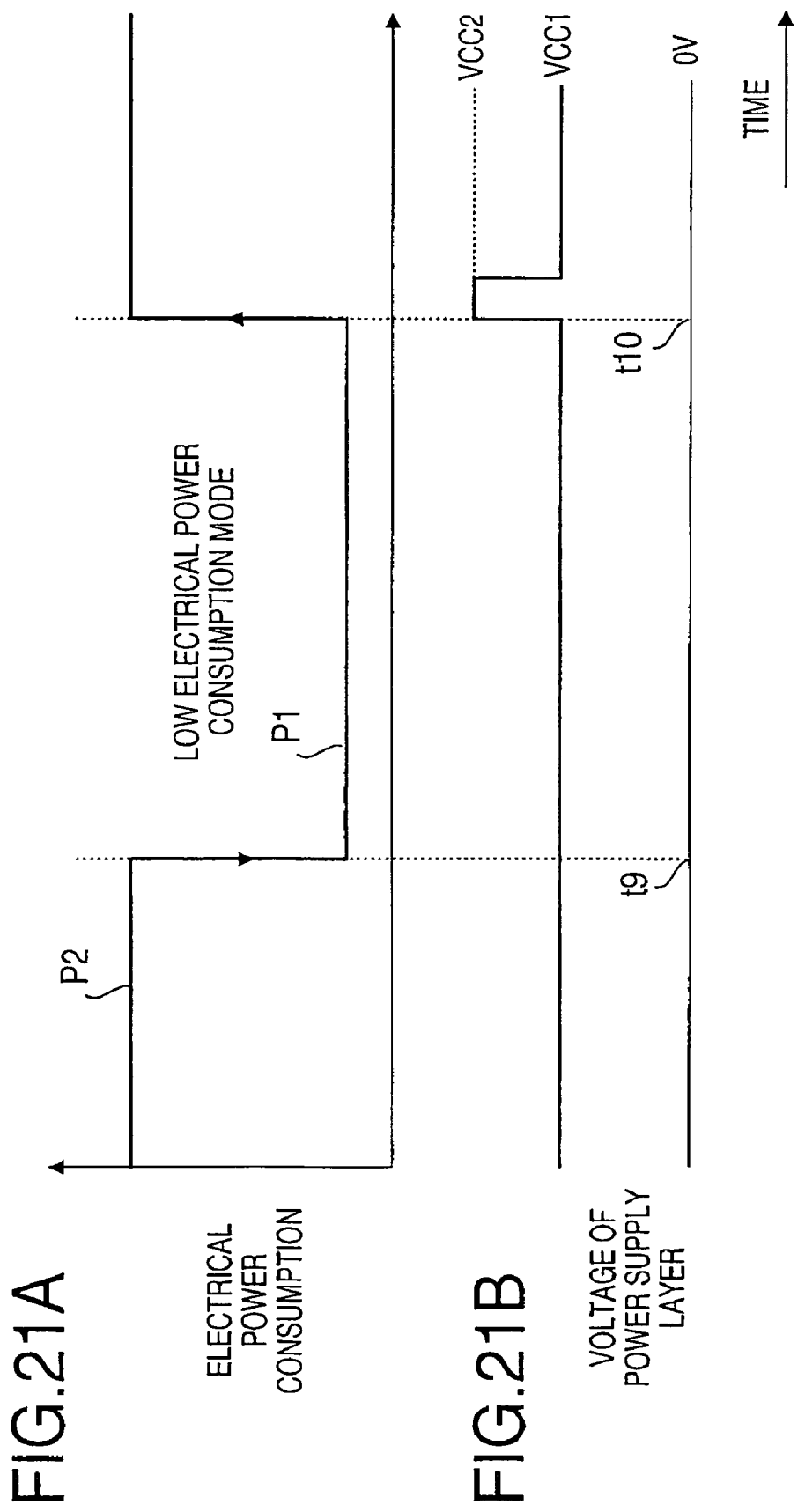
Figure 22:
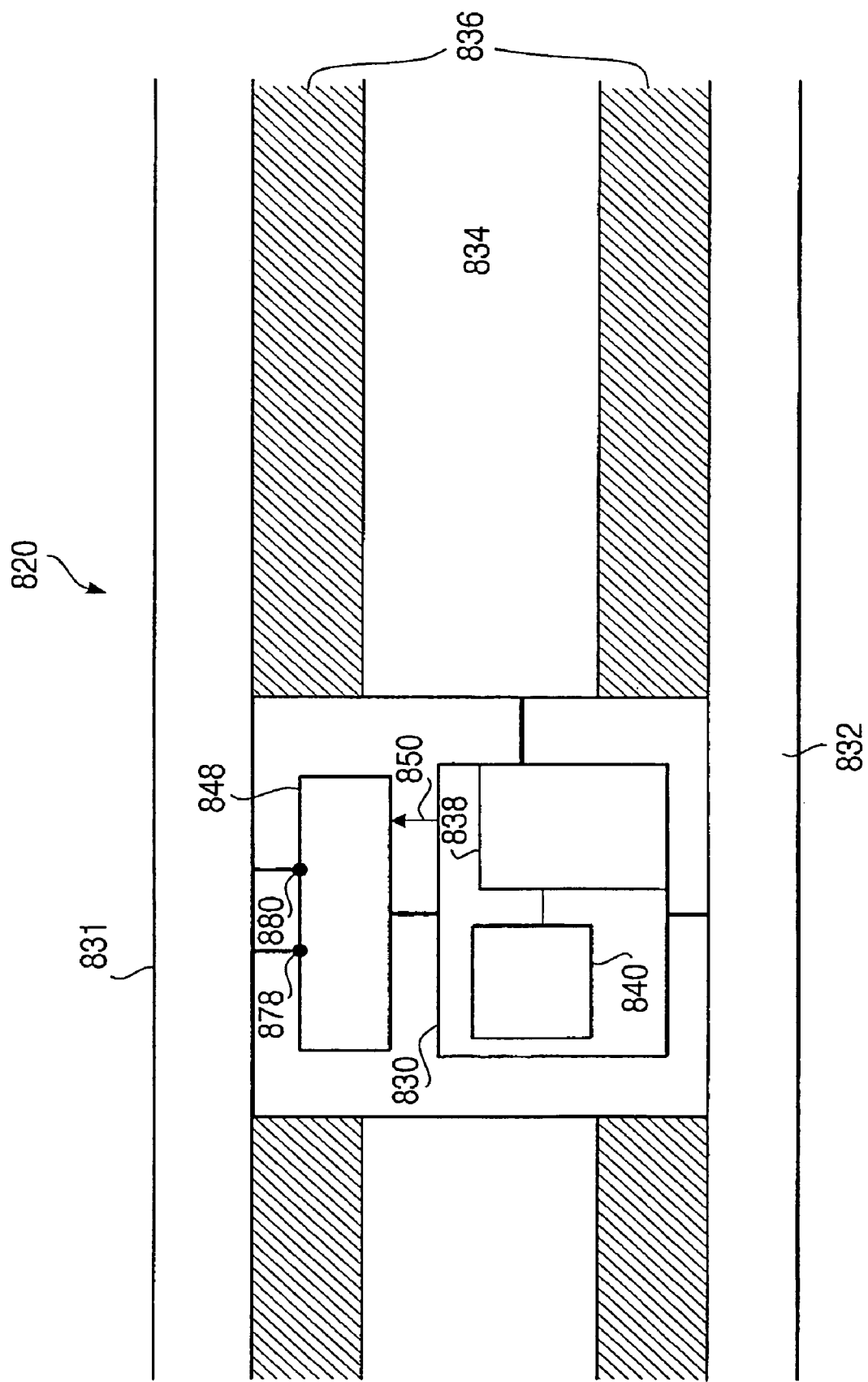
Figure 23:
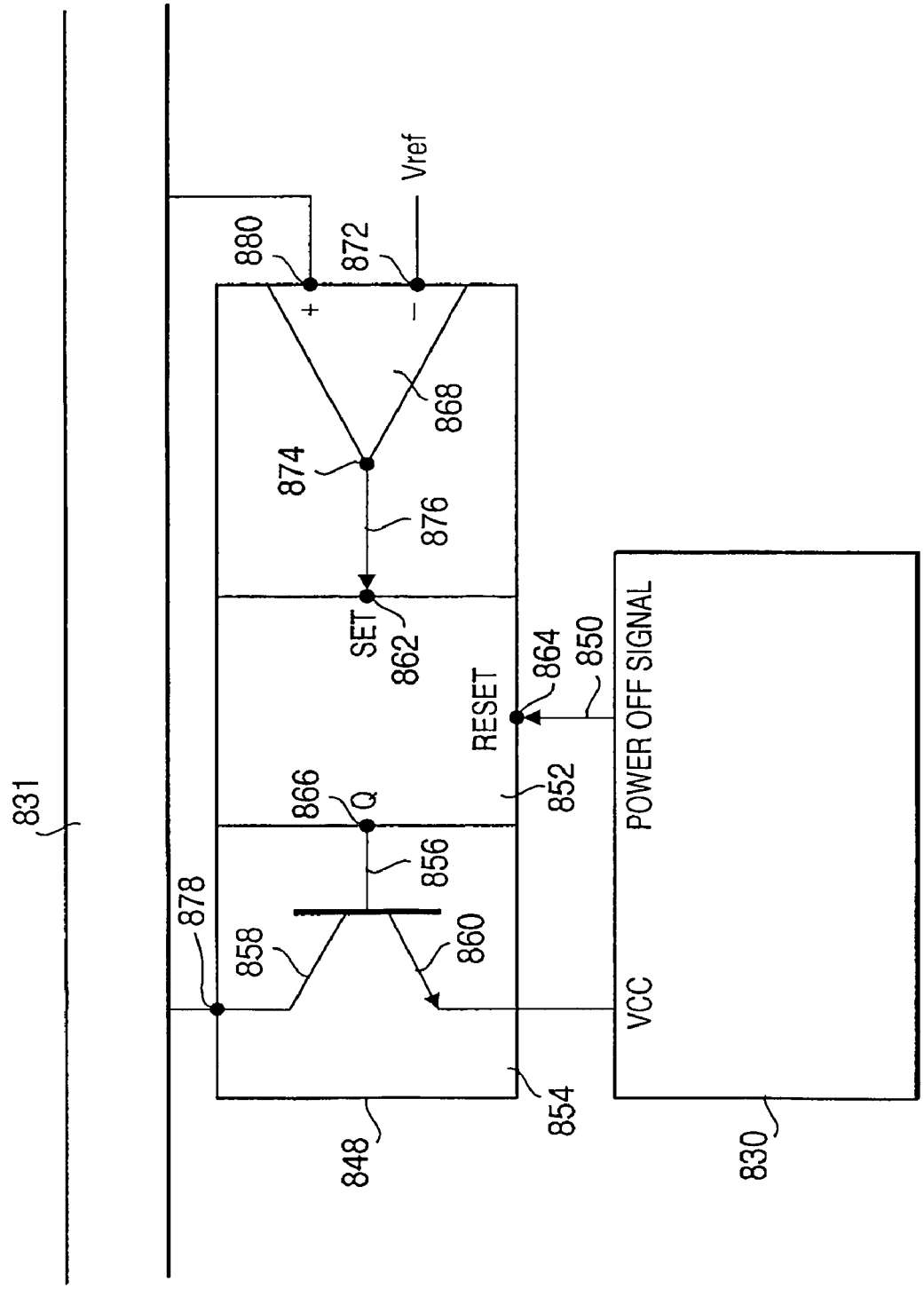

FIGS. 14A, 14B, and 14C show the relationship in time domain among the electrical power consumption level of the device, a power off signal, and a trigger signal in the second embodiment;

FIG. 15 shows a cross-sectional structure of a 2D-DST board of a signal communication apparatus in a third embodiment;

FIGS. 16A, 16B, and 16C show the relationship in time domain among the electrical power consumption level of a device, the transmission signal, and a trigger signal in the third embodiment;

FIG. 17 shows a cross-sectional structure of a 2D-DST board of a signal communication apparatus in a fourth embodiment;

FIG. 18 is a detailed drawing around a power supply switch circuit and a device shown in FIG. 17 in the fourth embodiment;

FIGS. 19A, 19B, 19C, and 19D show the relationship in time domain among the electrical power consumption level of the device, a power off signal, a trigger detecting signal, and the transmission signal in the fourth embodiment;

FIG. 20 shows a cross-sectional structure of a 2D-DST board of a signal communication apparatus in a fifth embodiment;

FIGS. 21A and 21B show the relationship in time domain between the electrical power consumption level of a device and the voltage of a power supply layer in the fifth embodiment;

FIG. 22 shows a cross-sectional structure of a 2D-DST board of a signal communication apparatus in a sixth embodiment;

FIG. 23 is a detailed drawing around a power supply switch circuit and a device shown in FIG. 22 in the sixth embodiment;

FIGS. 24A and 24B show the relationship in time domain between the electrical power consumption level of the device and the voltage of a power supply layer in the sixth embodiment; and FIGS. 25A and 25B show the relationship in time domain between the electrical power consumption level of a device and the transmission signal.

DETAILED DESCRIPTION OF THE EMBODIMENTS

An operation control method of a signal communication apparatus and signal communication devices (2D-DST devices) according to each of embodiments of the present invention is considered applicable to clothing provided with an antenna function that receives an image signal outputted from a capsule endoscope. The clothing provided with an antenna function includes circuits incorporated therein for obtaining information on a physical condition and/or a body cavity image of a patient putting thereon without using a wired cable or a copper film pattern. In addition, the clothing provides more excellent flexibility and durability, and allows reducing the weight and design limitation thereof, more densely incorporating antennas therein, and obtaining an image signal with a higher S/N ratio. Referring to the accompanying drawings, configurations and operations of endoscope systems, each of which includes such clothing provided with an antenna function, will be explained.

Figure 1:
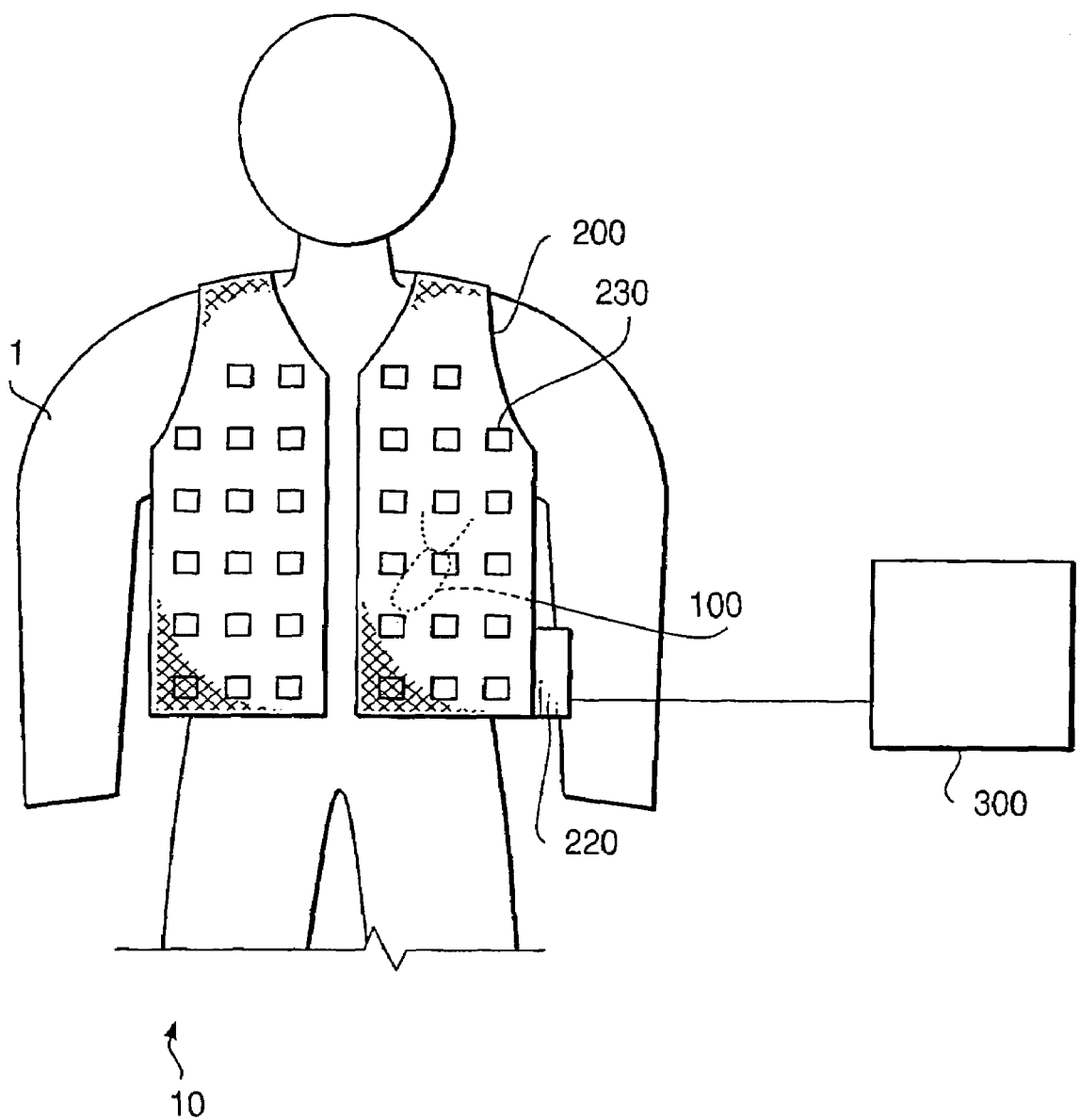

FIG. 1 schematically shows the configuration of an endoscope system 10 according to the present invention. By the endoscope system 10 shown in FIG. 1, information on the physical condition and/or a body cavity image of a patient 1 is acquired, so as to conduct diagnosis on the patient 1. The endoscope system 10 includes a capsule endoscope 100, a jacket 200 (signal communication apparatus) provided with an antenna function, and a PC 300 with a monitor. The capsule endoscope 100 is an inspection device for internal use that is put into the body cavity of the patient 1. The jacket 200 provided with an antenna function, which is wore by the patient 1, is provided with a function to receive image information outputted from the capsule endoscope 100. The PC 300 with the monitor is configured to display the image information obtained by the jacket 200 provided with the antenna function on the monitor.

The jacket 200 with the antenna function, which is shaped so as to cover a part of the body of the patient 1, has a plurality of devices 230 scattered therein. The plurality of devices 230 are 2D-DST devices, each of which may include various functions such as a function of obtaining the image signal outputted from the capsule endoscope 100, a function of sending out electromagnetic wave for providing an electrical power to the capsule endoscope 100 and/or a control signal, and a function of obtaining the information on the physical condition of the patient 1. Hereinafter, such a 2D-DST device is simply referred to as a device. In this case, each of the plurality of devices 230 is provided with the function of obtaining the image signal outputted from the capsule endoscope 100 and the function of sending out electromagnetic wave for providing electrical power to the capsule endoscope 100 and/or a control signal. In addition, the jacket 200 includes a control unit 220 attached thereto so as to be located around the waist of the patient 1 while being put on, which controls the whole of the circuits.

Figure 2:
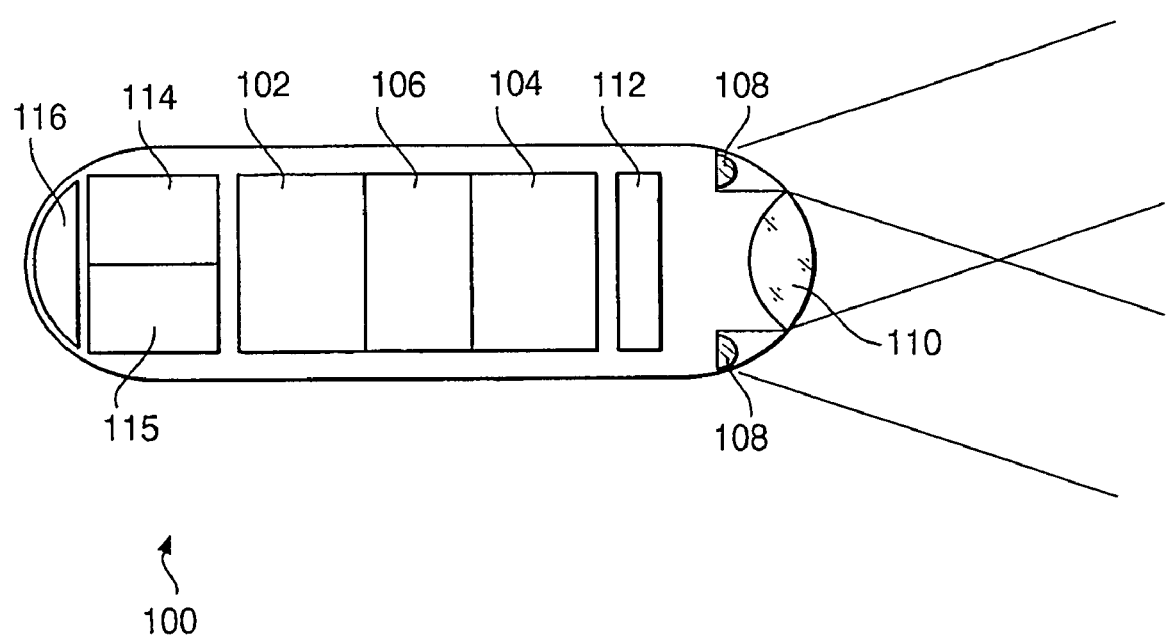

FIG. 2 shows the configuration of the capsule endoscope 100. The capsule endoscope 100 is configured very small, so as to easily go into an elongated serpentine bowel and take an image of the inside thereof. The capsule endoscope 100 is configured with a power supply portion 102 that supplies electrical power to each of constituents thereof, a controlling portion 104 that controls the whole thereof, a memory 106 that stores various data, two illuminating portions 108 that illuminate the body cavity, an objective optical system 110 for observing the body cavity, a solid-state image sensor 112 that takes an image of the body cavity, a transmitting portion 114 that sends out a radio wave to external devices, a receiving portion 115 that receives a radio wave from external devices, and an antenna portion 116 for sending to and receiving from the external devices.

When the capsule endoscope 100 is put into the body cavity of the patient 1 with the power supply portion 102 being powered on, the body cavity is illuminated by the illuminating portion 108. Illuminating light reflected by a reflecting surface such as a wall of the body cavity is incident to the objective optical system 110, and is received by a light receiving surface of the solid-state image sensor 112 that is provided on a focal plane at the imaging side of the objective optical system 110. The solid-state image sensor 112 photo-electrically-converts the received light to generate an image signal. The controlling portion 104 controls the transmitting portion 114, so that the generated image signal is modulated to be superimposed on a signal with a predetermined frequency, and is then transmitted to the external via the antenna portion 116. The transmitted image signal is received by the jacket 200 with the antenna function. In addition, the receiving portion 115 is configured to receive a radio wave from an external device. The controlling portion 104 takes on-off control of the illuminating portion 108 and drive control of the capsule endoscope 100.

Next, the configuration and operation of a 2D-DST circuit incorporated in the jacket 200 with the antenna function will be described.

Figure 3:
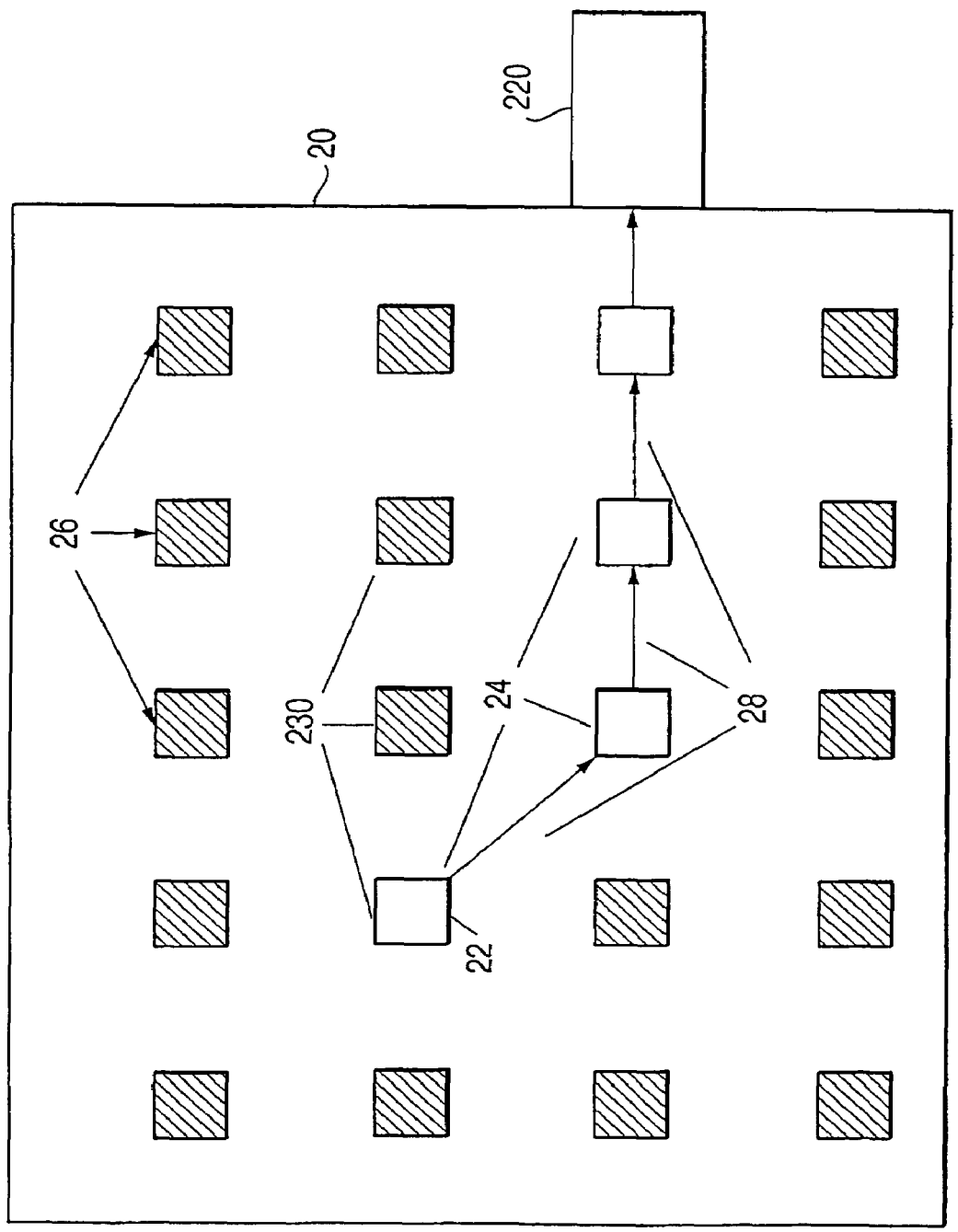

FIG. 3 schematically shows a 2D-DST board 20 applied to the jacket 200 with the antenna function. The 2D-DST board 20 is provided with the plurality of devices 230 and the control unit 220. The device 230 is configured to receive an image signal from the capsule endoscope 100 and transmit the received signal to a predetermined destination (in this case, to the control unit 220). The control unit 220 comprehensively controls the whole of the 2D-DST board 20. It is noted that in the 2D-DST board 20 shown in FIG. 3, ones contributing to signal transmission among the plurality of devices are indicated by white squares, and are referred to as "transmission devices 24", for the sake of convenience. In addition, the other devices not contributing to signal transmission are indicated by shaded squares, and are referred to as "non-transmission devices 26". Further, at least one of the devices that actually receive an image signal from the capsule endoscope 100 is referred to as a "receiving device 22". The receiving device 22 also functions as a transmission device.

In the aforementioned configuration, for example, a single device (in this case, the receiving device 22) is selected as a device for receiving an image signal from the capsule endoscope 100. When the receiving device 22 is selected, the control unit 220 determines transmission devices 24 for transmitting a signal to be received to the control unit 220 and a transmission channel 28. Based on the determination, the signal received by the receiving device 22 is transmitted to the control unit 220 via the transmission devices 24 by means of a predetermined algorism. At this time, the non-transmission devices 26 do not contribute to signal transmission, yet the power supply thereof is set on. Operation mode of the transmission devices 24 and the non-transmission devices 26 at this time is referred to as a "normal mode" for the sake of convenience. In the normal mode, sufficient electrical power is supplied to each of the devices 230. Therefore, each of the devices 230 in the normal mode can carry out all the functions thereof. According to the present invention, for instance, electrical power saving of the whole of the signal communication apparatus is achieved by reducing electrical power consumption of these devices 230.

Figure 4:
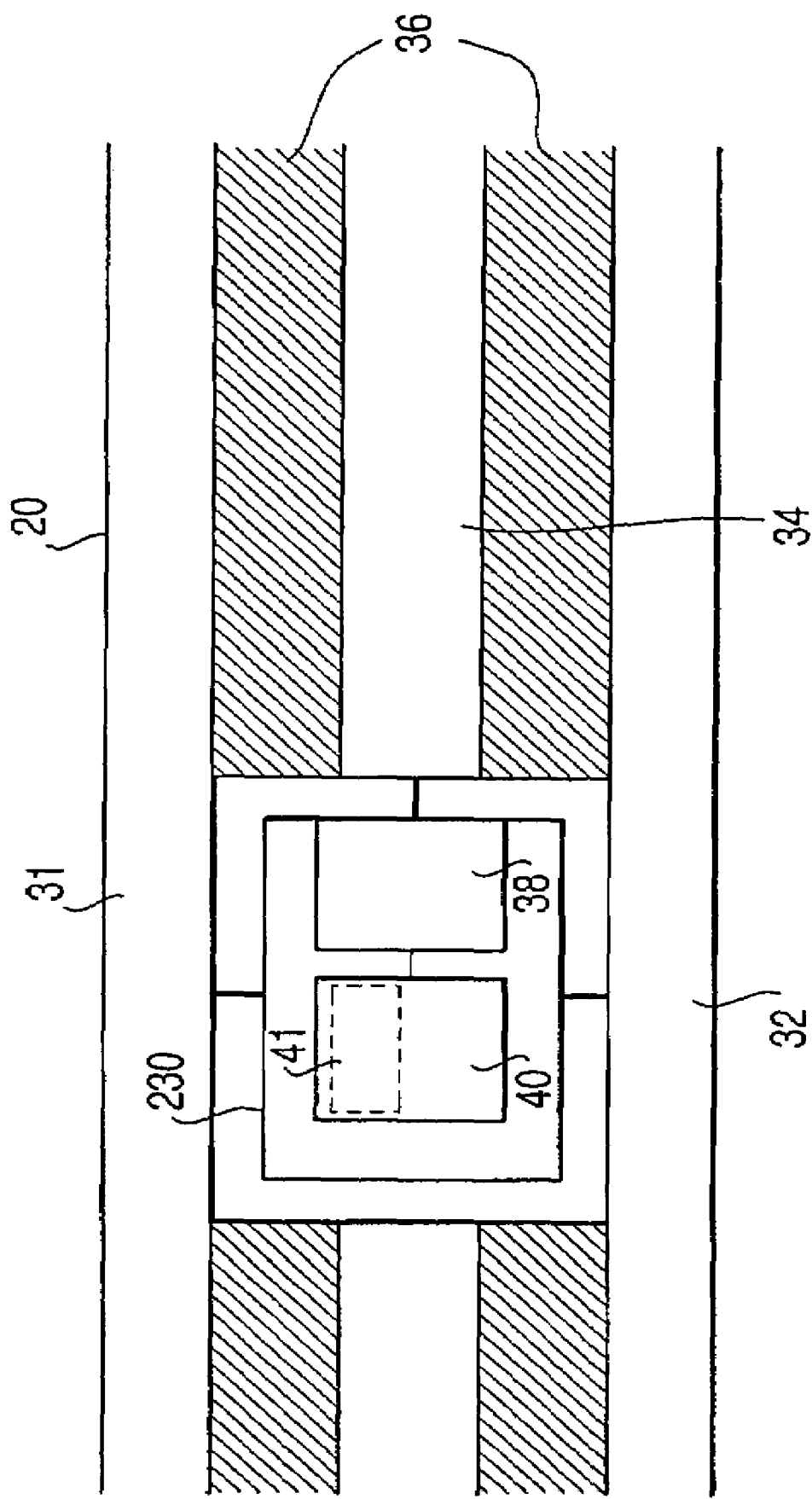

FIG. 4 schematically shows a basic cross-sectional structure of the 2D-DST board 20. The 2D-DST board 20 is configured using the principle of the communication apparatus disclosed in Japanese Unexamined Patent Publication No. 2003-188882, and all of 2D-DST boards of communication apparatuses described below are configured based on this structure.

The 2D-DST board 20 shown in FIG. 4 is provided with the devices 230, a power supply layer 31 that supplies electrical power to the devices 230, a ground layer 32 for grounding the devices, a signal layer 34 through which a signal is transmitted from one of the devices 230 to another, and insulating layers 36 that electrically isolate the signal layer 34, the power supply layer 31, and the ground layer 32 from each other. Each of the devices 230 includes a communicating part 38 for sending and receiving a signal between itself and any adjacent ones thereto, and a processing part 40 that carries out various kinds of processes, such as a process for generating a transmission signal transmitted among the devices 230 as described below. In addition, the processing part 40 includes an antenna portion 41 configured to receive an image signal outputted from the capsule endoscope 100.

According to the present invention, there are two modes for reducing the electrical power consumption of the devices 230. One of the two modes is a "low electrical power consumption mode (sleep mode)", which is a mode where the electrical power consumption of the devices 230 is reduced by setting functions of the devices 230 excluding minimum necessary functions thereof to be powered off with internal software processing. The other is a "power off mode", which is a mode where electrical power supply to the devices 230 is shut down by cutting the electrical connection between the devices 230 and the power supply layer 31. In the power off mode, only limited functions such as necessary functions of the communicating part 38 and other parts are driven by a battery inside each of the devices 230. A detailed explanation on these modes will be given below. Each of the devices 230 is configured to get back in the normal mode from these modes by external interrupt. It should be noted that the configuration of the 2D-DST board 20 shown in FIG. 4 is just one example, and that other variations may be applied.

Next, a process for setting a transmission channel of a signal to be transmitted in the 2D-DST board 20 will be explained.

Figure 5:
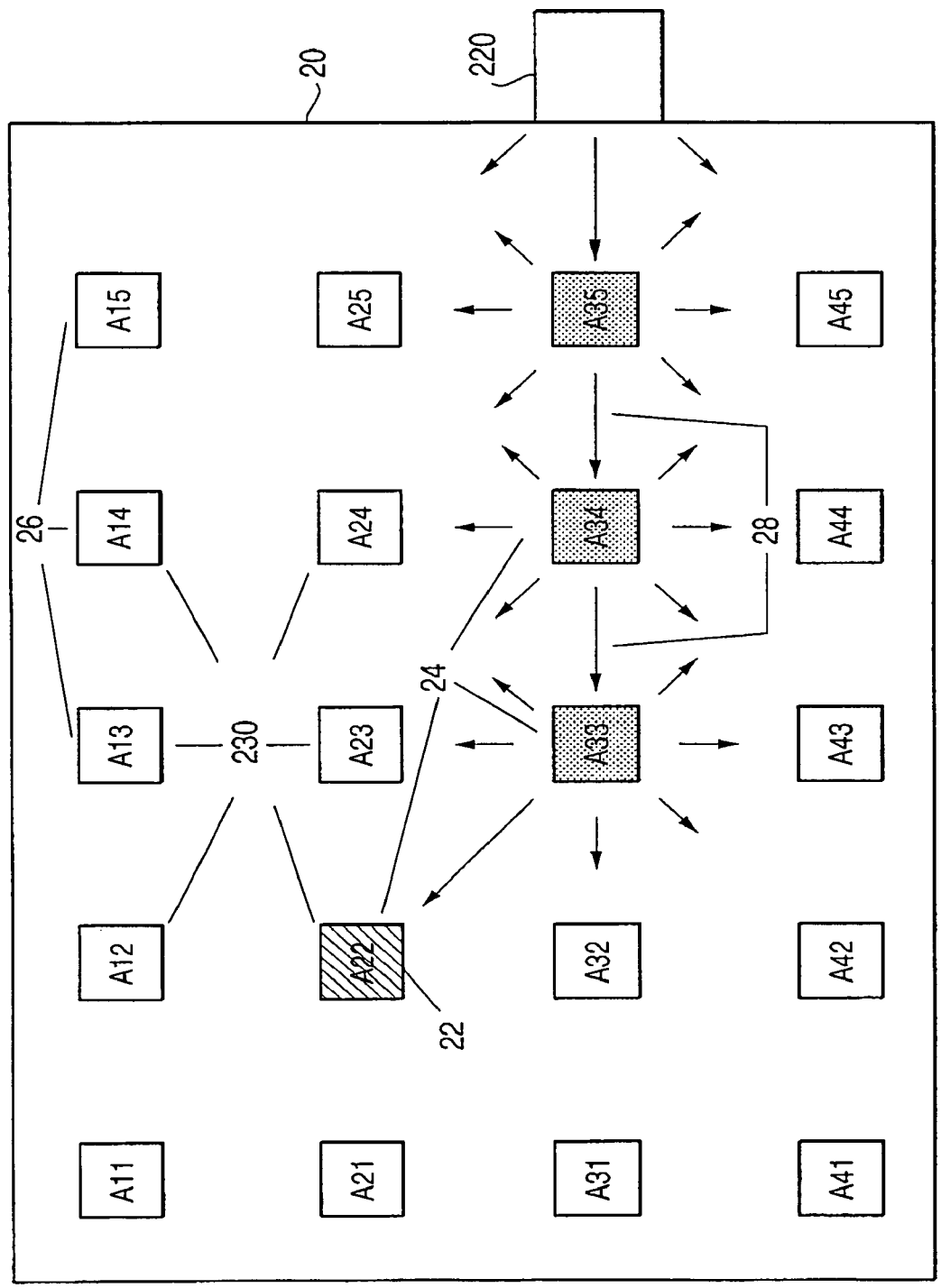
FIG. 5 is a figure illustrating a transmission channel of a transmission channel setting signal on the 2D-DST board.

As shown in FIG. 5, the devices 230 are arranged in a matrix on the 2D-DST board 20. Each of the devices 230 is given its own ID code in sequence from A11 to A45 according to the row and column locations thereof, so as to be identified. The ID code is managed by the control unit 220.

When an image signal from the capsule endoscope 100, for example, is received by the receiving device 22, the receiving device 22 is set as the first device that transmits a transmission signal (i.e., the source of the transmission channel). The control unit 220 receives the information that the device A22 is the receiving device 22, and then determines the transmission channel 28 and the transmission devices 24 based on the information. The transmission channel 28 is generally determined such that transmission distance becomes the shortest or the number of the transmission sites, i.e., the transmission devices 24 becomes the minimum. However, it should be noted that other methods to determine the transmission channel may be applied.

Figure 6:
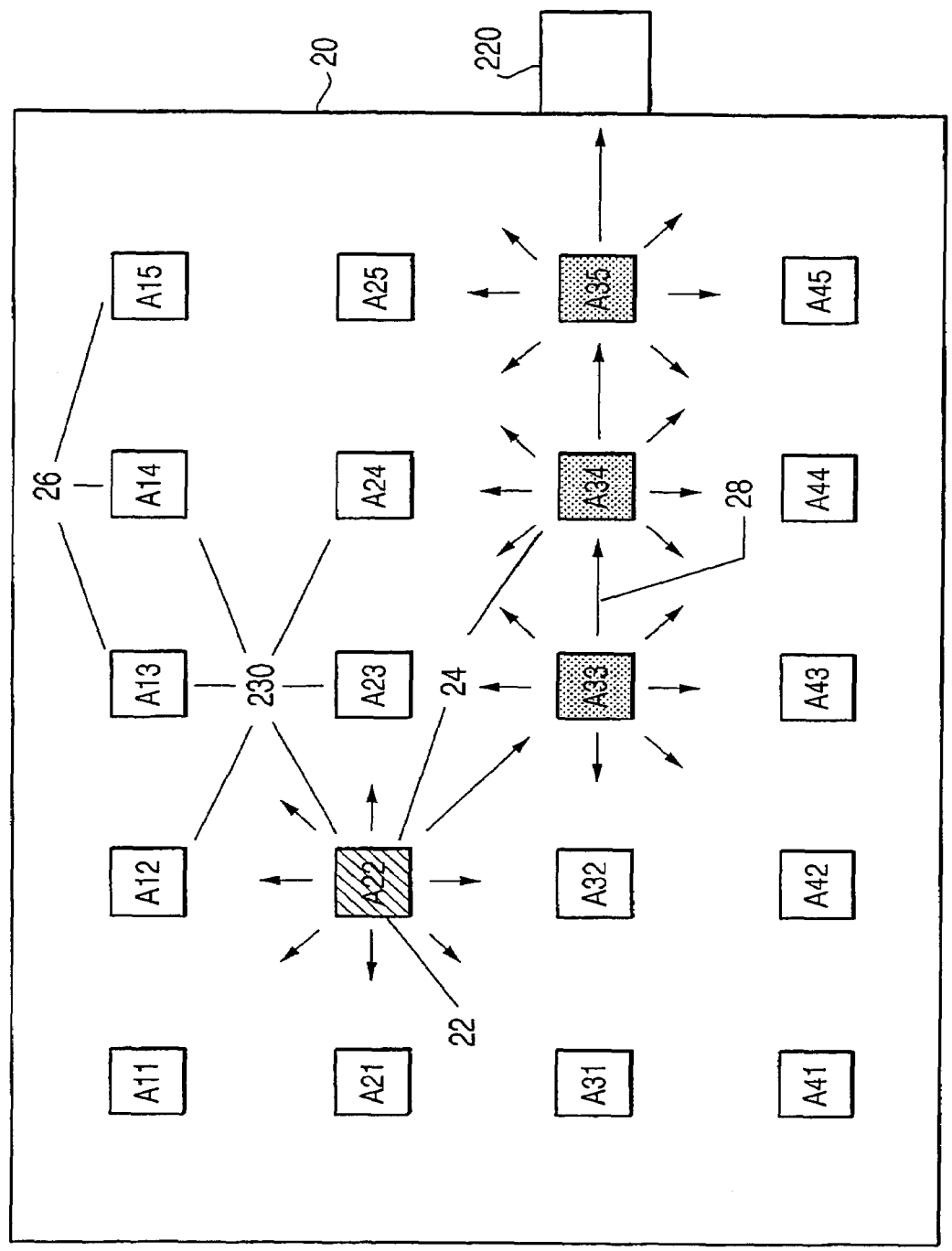
FIG. 6 is a figure illustrating a transmission channel of a transmission signal from a receiving device to a control unit.

FIG. 6 is a figure illustrating the transmission channel of the transmission signal from the receiving device 22 to the control unit 220. The device A22 is set as the first device that transmits the transmission signal, and then devices A33, A34, and A35 on the transmission channel 28 are set as transmission devices 24. The transmission signal is transmitted from the device A22 to the control unit 220 along the transmission channel 28. The transmission signal includes a data with a configuration of "(a command)+(A33)+(A34)+(A35)". The command, for instance, includes information that the received signal will be transmitted to the control unit 220. ID codes added to the command, for example, represent the ID codes of the transmission devices 24. There may be various kinds of commands corresponding to various purposes, in addition to the above command.

Next, a process for setting the transmission channel 28 will be described with reference to a flowchart.

Figure 7:
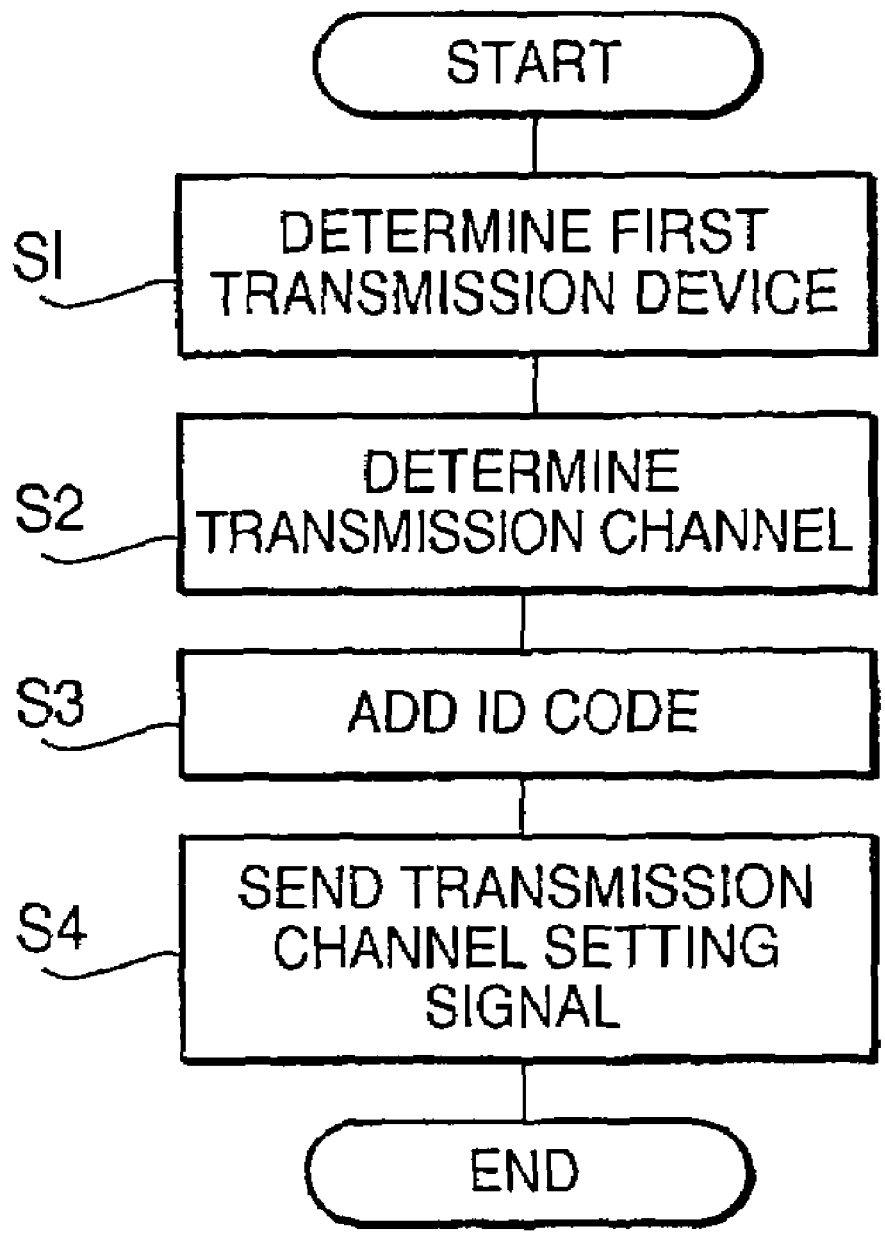
FIG. 7 is a flowchart illustrating a process for setting the transmission channel of the transmission signal.

FIG. 7 is a flowchart illustrating a process for setting the transmission channel 28. First, the first device (in this case, the device A22) that transmits the transmission signal is determined (S1). Thereafter, the control unit 220 chooses the transmission channel 28 and the transmission devices 24, and confirms the ID codes of the transmission devices 24 (S2). In this case, the ID codes of the transmission devices 24 are identified as A33, A34, and A35, respectively.

Next, the devices A33, A34, and A35 have to be made recognize that they themselves have been defined as the transmission devices 24. A transmission channel setting signal for making the devices A33, A34, and A35 have such a recognition is transmitted from the control unit 220 to the devices A33, A34, and A35. The control unit 220 adds, to the transmission channel setting signal, ID codes of the first device (the device A22) that transmits the transmission signal and the transmission devices 24 (the devices A33, A34, and A35) (S3). More specifically, the transmission channel setting signal includes a data with a configuration of "(a command)+(A22)+(A33)+(A34)+(A35)". The command, for instance, includes an instruction for making the corresponding devices recognize that they have been chosen as the transmission devices 24. The ID codes added to the command represent the ID codes of the chosen devices. In this case, for example, as the order for an ID code to be added to the command is more backward, the added ID code represents the ID code of a device closer to the control unit 220. The control unit 220 then transmits the transmission channel setting signal (S4). Thereby, the transmission channel setting signal is transmitted on the 2D-DST board 20 by the 2D-DST technology. After S4, the control unit 220 terminates a series of processes shown in this flowchart.

Each of the devices, which have received the transmission channel setting signal from the control unit 220, judges whether its own ID code is included in the transmission channel setting signal or not with reference to the transmission channel setting signal. According to the present invention, the adjacent devices to the control unit 220, including the device A35, carry out the judging process. The devices, which have not judged that their own ID codes are included in the transmission channel setting signal, then take no following process. In contrast, the device A35 judges that its own ID code is included in the transmission channel setting signal, so as to identify itself as a device on the transmission channel 28. Next, the device A35 sends the transmission channel setting signal to the adjacent devices thereto. Each of the devices, which have received the transmission channel setting signal from the device A35, judges, in the same way as aforementioned, whether its own ID code is included in the transmission channel setting signal. Here, the adjacent devices to the device A35, including the device A34, carry out the judging process. The devices, which have not judged that their own ID codes are included in the transmission channel setting signal, then take no following process. In contrast, the device A34 judges that its own ID code is included in the transmission channel setting signal to identify itself as a device on the transmission channel 28. Thereafter, the device A34 sends out the transmission channel setting signal to the adjacent devices thereto.

Each of the devices, which have received the transmission channel setting signal from the device A34, judges, in the same way as described above, whether its own ID code is included in the transmission channel setting signal. Here, the adjacent devices to the device A34, including the device A33, carry out the judging process. The devices, which have not judged that their own ID codes are included in the transmission channel setting signal, then take no following process. In contrast, the device A33 judges that its own ID code is included in the transmission channel setting signal to identify itself as a device on the transmission channel 28. Thereafter, the device A33 sends out the transmission channel setting signal to the adjacent devices thereto.

Each of the devices, which have received the transmission channel setting signal from the device A33, judges, in the same way as described above, whether its own ID code is included in the transmission channel setting signal. Here, the adjacent devices to the device A33, including the device A22, carry out the judging process. The devices, which have not judged that their own ID codes are included in the transmission channel setting signal, then take no following process. In contrast, the device A22 judges that its own ID code is included in the transmission channel setting signal to identify itself as a device on the transmission channel 28. The transmission channel is thus determined, so that signal transmission using the 2D-DST technology is started. It is noted that the above transmission channel of the transmission channel setting signal is shown in FIG. 5.

Next, processes will be explained, in each of which the device on the 2D-DST board is set into the low electrical power consumption mode (sleep mode) or in the power off mode. It is noted that, during the operation of the jacket 200 provided with the antenna function, each of the devices is always being operated in the normal mode in the case where it is not being operated in the low electrical power consumption mode or the power off mode. It is further noted that such operation mode transition between the normal mode and the low electrical power consumption mode or power off mode may be achieved by employing the below-mentioned 2D-DST boards of the signal communication apparatuses in addition to the 2D-DST board 20 shown in FIG. 4.

When the device on the 2D-DST board has not received the transmission signal including its own ID code for more than a predetermined time period, it is set into the low electrical power consumption mode by internal software processing, or in the power off mode where electrical power supply to a device is shut down.

Figure 8:
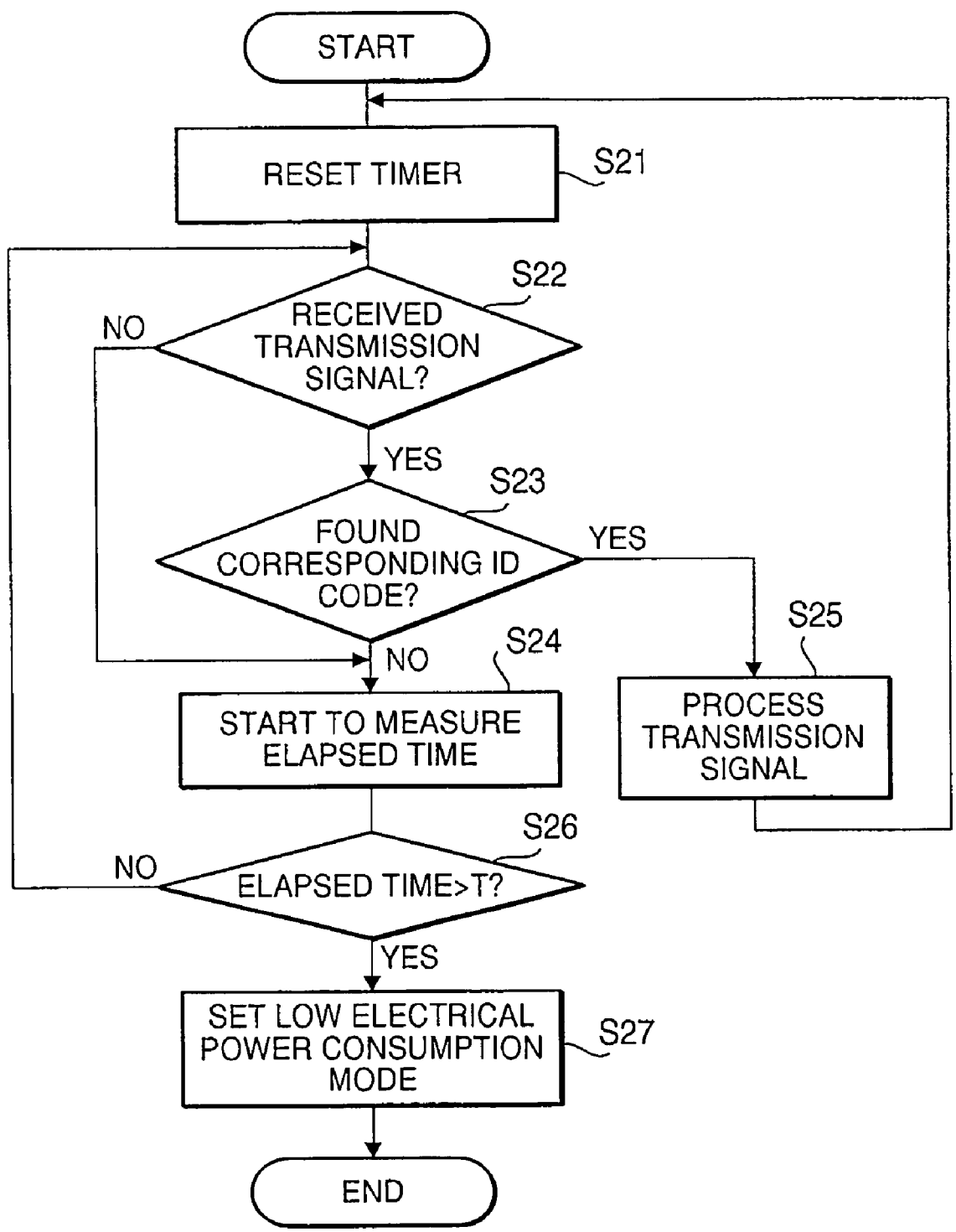
FIG. 8 is a flowchart showing a process in which a device on the 2D-DST board is set into a low electrical power consumption mode.

Next, a process will be explained, in which the device on the 2D-DST board is set into the low electrical power consumption mode. FIG. 8 is a flowchart showing a process in which the device on the 2D-DST board is set into the low electrical power consumption mode. The process shown in FIG. 8 is carried out by each of the devices on the 2D-DST board.

When the receiving device 22 and the transmission channel 28 are determined, and the receiving device 22 then starts to receive an image signal from the capsule endoscope 100, a timer of each of the devices is reset (S21). Thereafter, each of the devices judges whether it has received a transmission signal (S22). When the device judges that it has not received the transmission signal (S22: NO), the timer starts to measure elapsed time (S24). On the other hand, when the device judges that it has received the transmission signal (S22:YES), it judges whether the transmission signal includes its own ID code (S23). It is noted that the command included in the transmission signal is one of commands except for the below-mentioned sleep command, and is concerned in transmission of the transmission signal.

When the device judges that the transmission signal includes its own ID code in S23 (S23:YES), it carries out the processing of the transmission signal as described in the command (S25). After carrying out the processing, the process of the device goes back to S21. When the device judges that the transmission signal does not include its own ID code (S23:NO), the timer starts to measure elapsed time (S24).

After S24, the device judges whether the elapsed time measured by the timer is more than a predetermined time period T (S26). When the device judges that the elapsed time is more than the predetermined time period T (S26:YES), it does not recognize that it has served as the receiving device 22 or one of the transmission devices for more than the predetermined time period T. Therefore, the device identifies itself as a device not concerned in transmission of the transmission signal, so that it is set into the low electrical power consumption mode (S27), then terminating the process of the flowchart. When the device does not judge that the elapsed time is more than the predetermined time period T (S26:NO), the process thereof goes back to S22, the aforementioned series of steps from S22 to S26 are carried out again. Thus, when the device has not received the transmission signal including its own ID code for more than the predetermined time period T, it is set into the low electrical power consumption mode.

Referring to the flowchart shown in FIG. 8, the case where the device is set into the low electrical power consumption mode has been described. It should be noted that the aforementioned process may be applied to the case of the power off mode. In addition, the aforementioned process may be a process in which the device is set into the low electrical power consumption mode according to whether it has received the transmission signal, without judging whether its own ID code is included in the transmission signal.

Next, referring to a flowchart shown in FIG. 9, another process in which the device on the 2D-DST board is set into the low electrical power consumption mode will be described. In this process, when the device receives a transmission signal including a sleep command and its own ID code, it is set into the low electrical power consumption mode by internal software processing.

Figure 9:
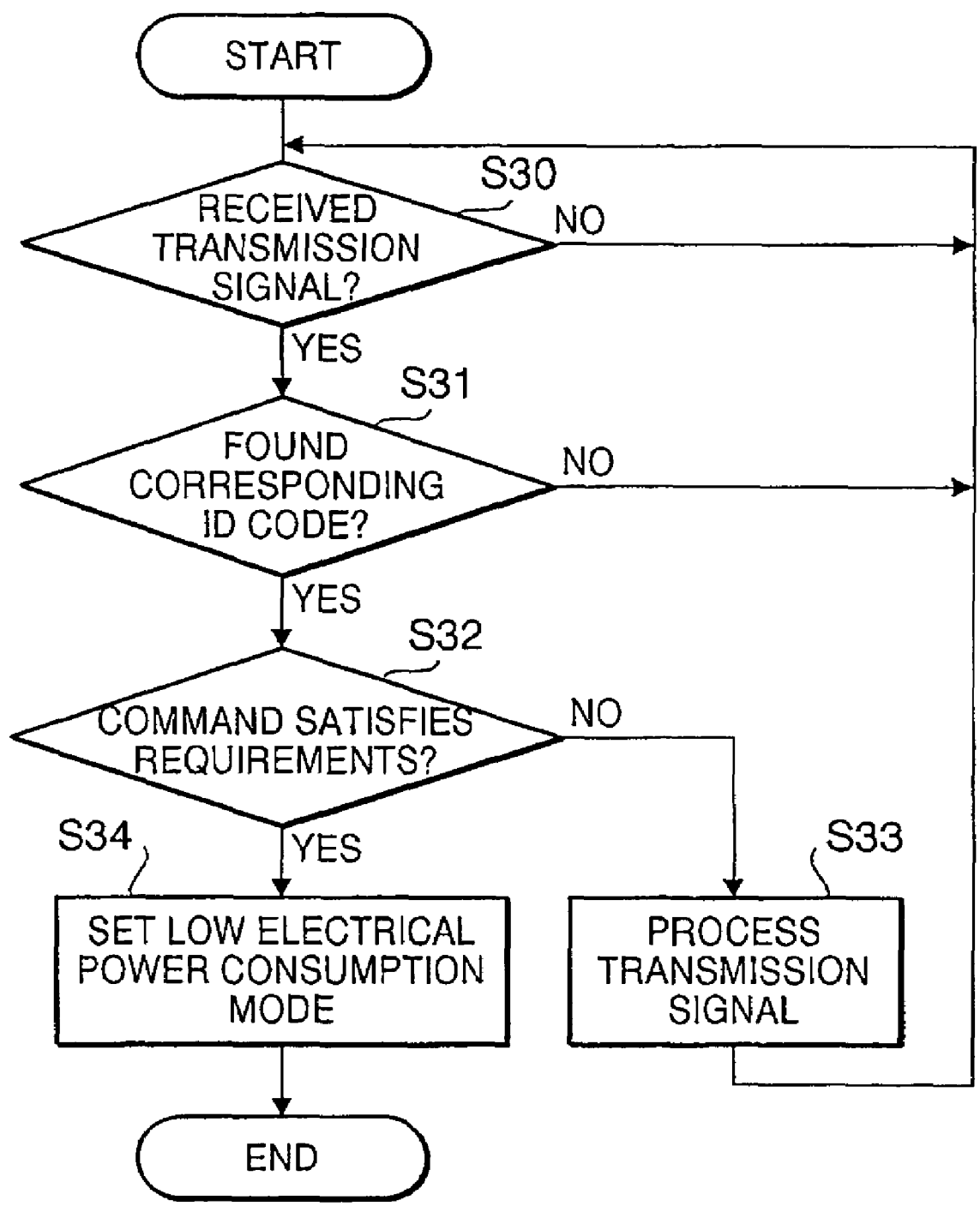
FIG. 9 is a flowchart showing another process in which the device on the 2D-DST board is set into the low electrical power consumption mode.

FIG. 9 is a flowchart showing a process in which a device on the 2D-DST board is set into the low electrical power consumption mode. When the receiving device 22 and the transmission channel are determined, and the receiving device 22 then starts to receive an image signal from the capsule endoscope 100, each of the devices judges whether it has received a transmission signal (S30). If it does not judge that it has received the transmission signal (S30:NO), the judging process will be carried out again after a predetermined time period. If it judges that it has received the transmission signal (S30:YES), it then judges whether the transmission signal include its own ID code (S31).

When the device does not judge that the transmission signal includes its own ID code (S31:NO), the process goes back to S30. In contrast, when the device judges that the transmission signal includes its own ID code (S31:YES), it then judges whether a command included in the transmission signal satisfies two requirements (S32) regarding the sleep command. One of the requirements is a requirement that the command is the sleep command for making the device set into the low electrical power consumption mode. The other is a requirement that the command informs that the ID code, which has been identified to correspond to the ID code of the device, designates the device to be set into the low electrical power consumption mode. If the command does not satisfy the above requirements (S32:NO), a process for the transmission signal described in the command will be executed. In contrast, if the command satisfies the above requirements (S32:YES), the device will be set into the low electrical power consumption mode (S34), then terminating the process of this flowchart. Hereinbefore, the process in which the device is set into the low electrical power consumption mode has been explained. It is noted that the process could be applied to the case of the power off mode.

Hereinbefore, the processes have been explained, in each of which the device is set into the low electrical consumption mode. Next, processes will be explained, in each of which a device being operated in the low electrical power consumption mode or power off mode is set back into the normal mode.

A signal communication apparatus in a first embodiment will be explained below. In the first embodiment, a trigger layer is provided in a 2D-DST board. In the following explanation of the first embodiment, a device being operated in the low electrical power consumption mode is set back into the normal mode.

Figure 10:
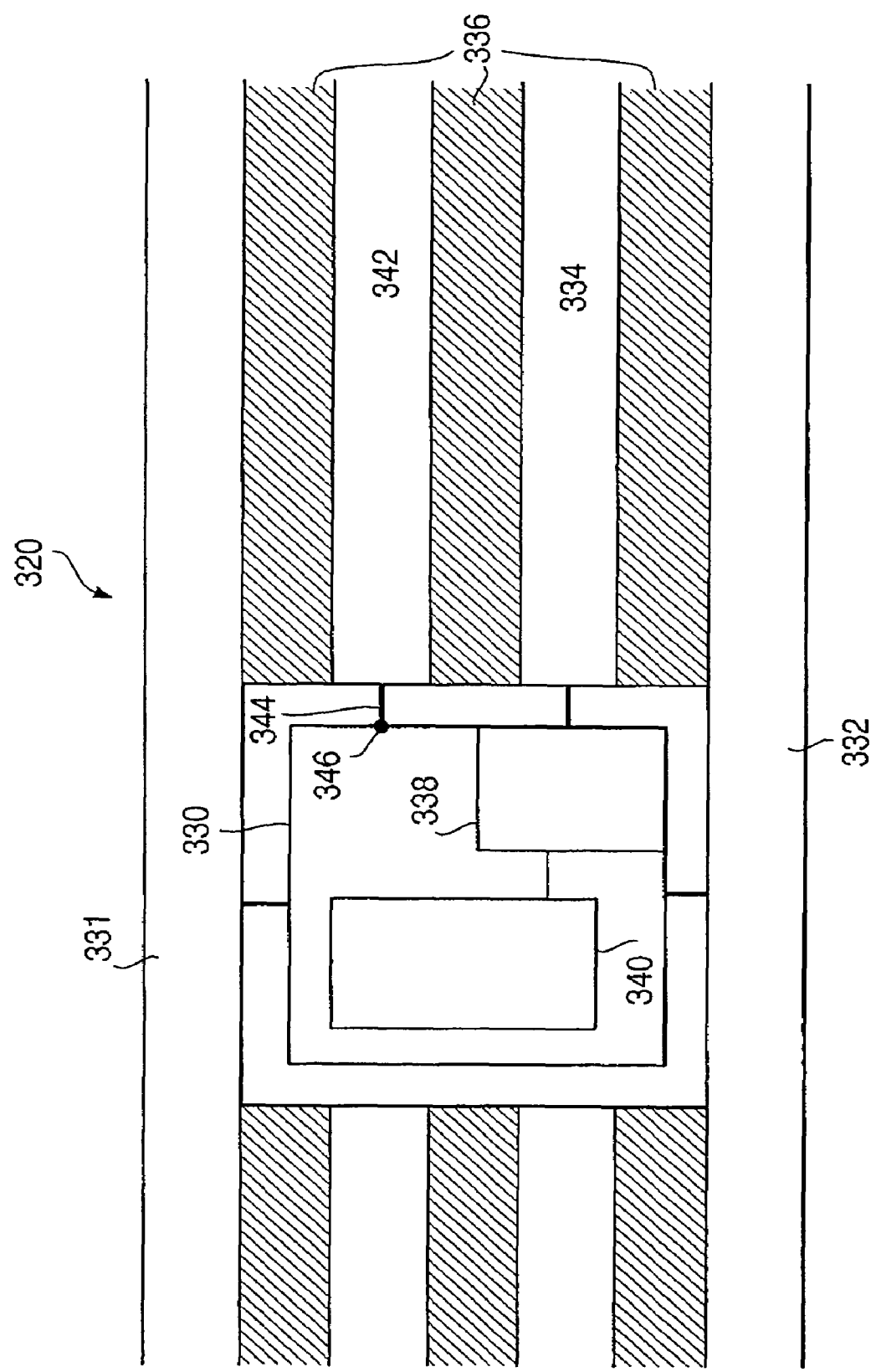
FIG. 10 shows a cross-sectional structure of a 2D-DST board of a signal communication apparatus in a first embodiment.

FIG. 10 shows a cross-sectional structure of a 2D-DST board 320 of a signal communication apparatus in the first embodiment. The 2D-DST board 320 is provided with devices 330, a power supply layer 331 that supplies electrical power to the devices 330, a ground layer 332 for grounding the devices 330, a trigger layer 342, a signal layer 334 through which the transmission signal is transmitted from one of the devices 330 to another, and insulating layers 336 that electrically isolate the conductive layers (the power supply layer 331, ground layer 332, signal layer 334, and trigger layer 342) from each other. Each of the devices 330 includes a communicating part 338 for sending and receiving the transmission signal between itself and any adjacent ones thereto, and a processing part 340 that includes an antenna portion (not shown) configured to receive an image signal outputted from the capsule endoscope 100 and also carries out various kinds of processes such as a process for generating the transmission signal. The trigger layer 342 is connected to a trigger terminal 346 provided at each of the devices 330. A trigger signal 344, which instructs each of the devices 330 in the low electrical power consumption mode to get back in the normal mode, is transmitted through the trigger layer 342. When the trigger signal transmitted through the trigger layer 342 is inputted to the trigger terminal 346, the device 330 is set back into the normal mode from the low electrical power consumption mode.

Figure 11:
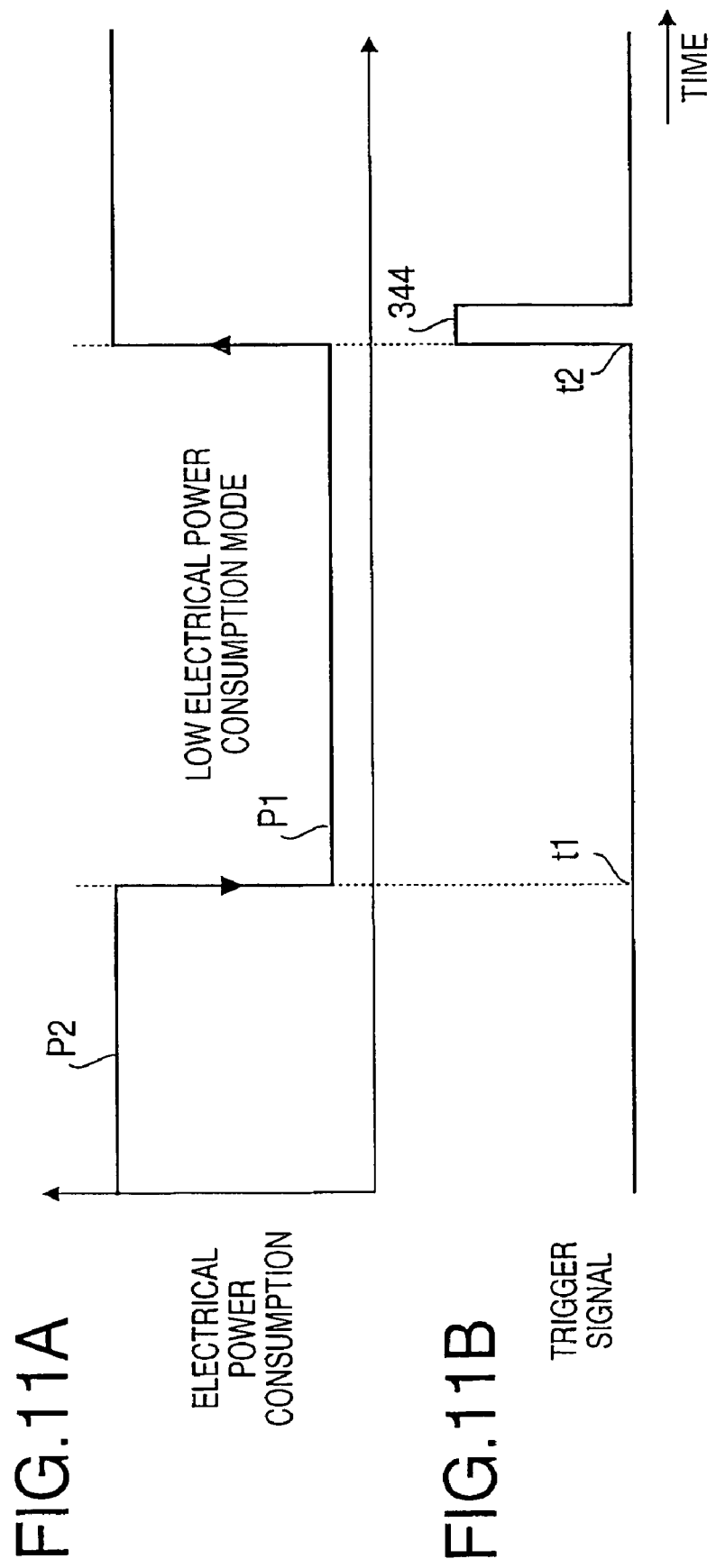
FIGS. 11A and 11B show the relationship in time domain between the electrical power consumption level of the device and a trigger signal in the first embodiment.

Here, it is assumed that the device 330 is being operated in the low electrical power consumption mode, that is, functions excluding minimum necessary functions thereof are being powered off. If the trigger signal 344, in such a state, is transmitted through the trigger layer 342 to be inputted to the device 330 from the control unit 220, the device 330 will be set back into the normal mode from the low electrical power consumption mode. FIGS. 11A and 11B show the relationship in time domain between the electrical power consumption level of the device 330 and the trigger signal 344.

FIG. 11A shows the change of the electrical power consumption level of the device 330 in time domain. The vertical axis of FIG. 11A represents the electrical power consumption level, and the horizontal axis does time. FIG. 11B shows the timing of the trigger signal 344 being generated. The device 330, which is being operated in the normal mode with an electrical power consumption level of P2, for instance, after keeping such an operation without finding its own ID number in the transmission signal for a predetermined time period, is set into the low electrical power consumption mode at a time of t1. The device 330 is thereby operated with an electrical power consumption level of P1. Then, at a time of t2, the device 330 receives the trigger signal 344 to get back in the normal mode from the low electrical power consumption mode. Thereby, the electrical power consumption level becomes P2 in the normal mode.

Next, a signal communication apparatus in a second embodiment will be explained. In the second embodiment, a 2D-DST board is provided with a trigger layer and power supply switch circuits. In this case, each of devices in the power off mode is set back into the normal mode.

Figure 12:
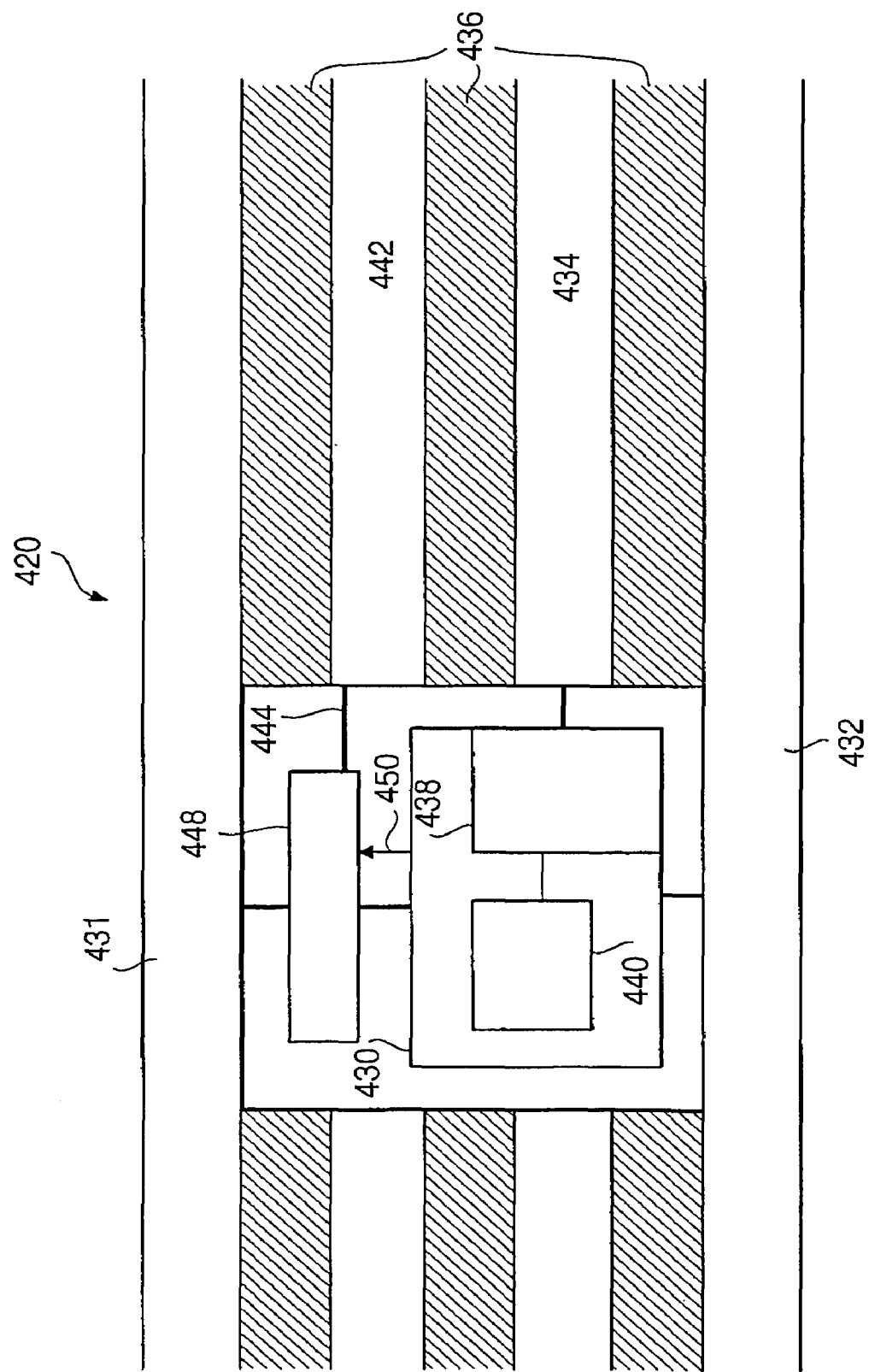
FIG. 12 shows a cross-sectional structure of a 2D-DST board of a signal communication apparatus in a second embodiment.

FIG. 12 shows a cross-sectional structure of a 2D-DST board 420 of a signal communication apparatus in the second embodiment. The 2D-DST board 420 is provided with devices 430, power supply switch circuits 448 for selecting supply or shutoff of electrical power to the respective devices 430, a power supply layer 431 that supplies electrical power to the devices 430 and the power supply switch circuits 448, a ground layer 432 for grounding the devices 430, a trigger layer 442, a signal layer 434 through which the transmission signal is transmitted from one of the devices 430 to another, and insulating layers 436 that electrically isolate the conductive layers (the power supply layer 431, ground layer 432, signal layer 434, and trigger layer 442) from each other. Each of the devices 430 includes a communicating part 438 for sending and receiving the transmission signal between itself and any adjacent ones thereto, and a processing part 440 that includes an antenna portion (not shown) configured to receive an image signal outputted from the capsule endoscope 100 and also carries out various kinds of processes in each of the devices 430. The trigger layer 442 is connected to the power supply switch circuit 448. A trigger signal 444, which instructs each of the devices 430 in the power off mode to get back in the normal mode, is transmitted through the trigger layer 442. When the power supply switch circuit 448 receives the trigger signal 444 transmitted through the trigger layer 442, the device 430 is set back into the normal mode from the power off mode. In the case where the device 430 is set into the power off mode from the normal mode, a power off signal 450 is outputted from the device 430 to the power supply switch circuit 448, so that such a mode transition is made.

Figure 13:
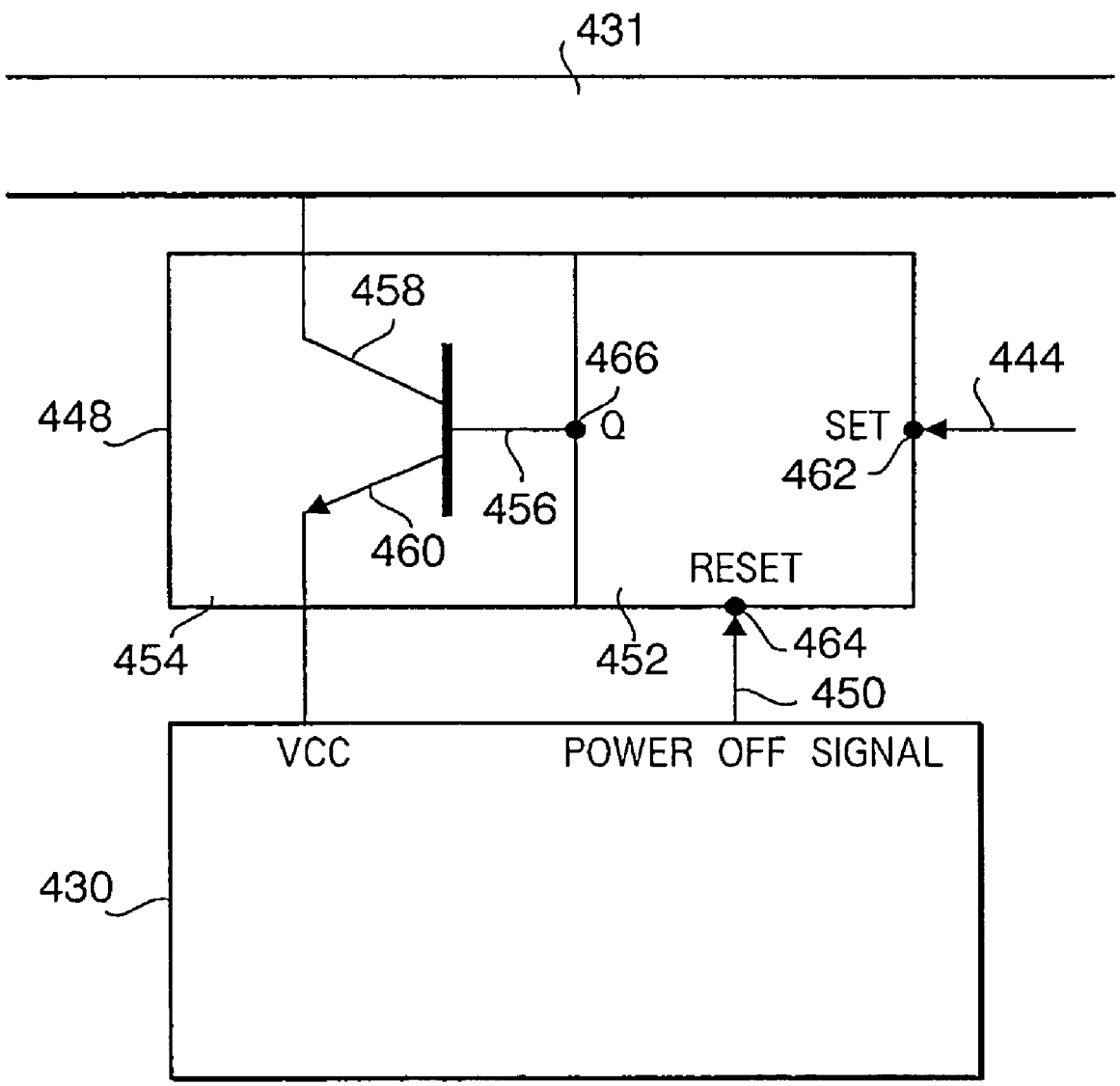
FIG. 13 is a detailed drawing around a power supply switch circuit and a device shown in FIG. 12 in the second embodiment.

FIG. 13 is a detailed drawing around the power supply switch circuit 448 and device 430 shown in FIG. 12. The power supply switch circuit 448 is provided with a flip-flop (F. F.) 452 and a transistor 454.

The flip-flop 452 is a switching means, which includes a first receiving terminal 462, a second receiving terminal 464, and an output terminal 466. The first receiving terminal is an input terminal for the trigger signal 444. The second receiving terminal is an input terminal for the power off signal 450 outputted from the device 430. The output terminal 466 is connected with the transistor 454, and provides on-off control of the transistor 454 based on the trigger signal 444 or the power off signal 450 to be inputted to the flip-flop 452.

The flip-flop 452 detects the trigger signal 444 to output a signal for controlling the electrical connection or cutting between the power supply layer 431 and the device 430 in the transistor 454. If the trigger signal 444 is inputted to the first receiving terminal 462 of the flip-flop 452, the output terminal 466 will be connected to the power supply (not shown) to output a predetermined voltage or more. In contrast, if power off signal 450 is inputted to the second receiving terminal 464, the electrical connection between the output terminal 466 and the power supply will be cut off. Thereby, electrical power supply to the output terminal 466 is shut off, or is reduced to a level less than the predetermined voltage.

The transistor 454 is a switching device, which is provided with a base terminal 456, a collector terminal 458, and an emitter terminal 460. The base terminal 456 is connected with the output terminal 466. The collector terminal 458 is connected with the power supply layer 431. The emitter terminal 460 is connected with the device 430. The transistor 454 controls the electrical connection or cutting between the power supply layer 431 and the device 430. In the transistor 454, when the predetermined voltage or more is inputted to the base terminal 456, the collector terminal 458 and the emitter terminal 460 are electrically connected with one another.

In the aforementioned configuration, if the trigger signal 444 is inputted to the first receiving terminal 462 while the device 430 is being operated in the power off mode, the flip-flop 452 will output the predetermined voltage or more to the output terminal 466. Since the output terminal 466 is connected with the base terminal 456, the predetermined voltage or more is applied to the base terminal 456. Therefore, the collector terminal 458 is electrically connected with the emitter terminal 460, so that electrical power is supplied from the power supply layer 431 to the device 430.

In addition, if the power off signal 450 is inputted to the second receiving terminal 464 while the device 430 is being operated in the normal mode, the flip-flop 452 will output less than the predetermined voltage to the output terminal 466. For this reason, the collector terminal 458 is not electrically connected with the emitter terminal 460, and thereby, electrical power supply from the power supply layer 431 to the device 430 is shut off. FIGS. 14A, 14B, and 14C show the relationship in time domain among the electrical power consumption level of the device 430, the power off signal 450, and the trigger signal 444.

FIG. 14A is a graph showing the change of the electrical power consumption level of the device 330 in time domain. The vertical axis of FIG. 14A represents the electrical power consumption level, and the horizontal axis thereof does time. FIG. 14B shows the timing of the power off signal 450 being generated. FIG. 14C shows the timing of the trigger signal 444 being generated. The device 430, which is being operated in the normal mode with an electrical power consumption level of P2, for instance, after keeping such an operation without finding its own ID code in the transmission signal for a predetermined time period, is set into the power off mode at a time of t3 with the power supply switch circuit 448 receiving the power off signal 450 from the device 430. Thereby, the electrical power consumption level becomes P0. Then, at a time of t4, the device 430 receives the trigger signal 444 to get back in the normal mode with an electrical power consumption level of P2 from the power off mode.

Next, a signal communication device in a third embodiment will be explained. In the third embodiment, a trigger signal is transmitted through a signal layer. In this case, each of devices in the low electrical power consumption mode is set back into the normal mode.

FIG. 15 shows a cross-sectional structure of a 2D-DST board 520 of a signal communication apparatus in the third embodiment. The 2D-DST board 520 is provided with devices 530, a power supply layer 531 that supplies electrical power to the devices 530, a ground layer 532 for grounding the devices 530, a signal layer 534 through which the transmission signal and a trigger signal are transmitted from one of the devices 530 to another, and insulating layers 536 that electrically isolate the conductive layers (the power supply layer 531, ground layer 532, and signal layer 534) from each other. Each of the devices 530 includes a communicating part 538 for sending and receiving the transition signal between itself and any adjacent ones thereto, and a processing part 540 that includes an antenna portion (not shown) configured to receive an image signal outputted from the capsule endoscope 100 and also carries out various kinds of processes in each of the devices 530. The signal layer 534 is connected with a trigger terminal 546 and a signal transmission terminal 547 provided by the device 530. The communicating part 538 receives the transmission signal via the signal transmission terminal 547. It is noted that, without the trigger terminal 546 being provided at the device 530, the device 530 may be configured such that the trigger signal 544 diverges inside the communicating part after the device 530 has received the trigger signal 544 via the signal transmission terminal 547. When the trigger signal included by the transmission signal is inputted to the device 530 via the trigger terminal 546, the device 530 is set back into the normal mode from the low electrical power consumption mode.

Here, it is assumed that the device 530 is being operated in the low electrical power consumption mode. Accordingly, functions excluding minimum necessary functions of the device 530 are being powered off. If the trigger signal 544, in such a state, is transmitted through the signal layer 534 to be inputted to the device 530 from the control unit 220 via the trigger terminal 546, the device 530 is set back into the normal mode from the low electrical power consumption mode. FIGS. 16A, 16B, and 16C show the relationship in time domain among the electrical power consumption level of the device, the transmission signal, and the trigger signal 544.

FIG. 16A is a graph showing the change of the electrical power consumption level of the device 530 in time domain. The vertical axis of FIG. 16A represents the electrical power consumption level, and the horizontal axis thereof does time. FIG. 16B shows the waveform of the transmission signal, transmitted through the signal layer 534, in time domain. FIG. 16C shows the timing of the trigger signal 544 being generated.

As shown in FIG. 16B, the transmission signal is a rectangular wave having substantially two flat voltage levels of H and L, which are lower than a predetermined voltage Vref. In contrast, the trigger signal 544 has a voltage level of T higher than Vref. The device 530 detects a higher voltage level than Vref (that is, a signal with a voltage of T) as a trigger signal 544. It is noted that a threshold for detecting the trigger signal may be set to be a voltage level other than Vref. For example, a different voltage level from voltages of H and L of the transmission signal may be detected as a trigger signal.

The device 530, which is being operated in the normal mode with an electrical power consumption level of P2, is set into the low electrical power consumption mode at a time of t5, for instance, after keeping such an operation without finding its own ID code in the transmission signal for a predetermined time period. Thereby, the electrical power consumption level becomes P1. Then, at a time of t6, the trigger signal 544 is detected, so that the device 530 gets back in the normal mode with an electrical power consumption level of P2 from the low electrical power consumption mode.

Next, a signal communication apparatus in a fourth embodiment will be explained. In the fourth embodiment as well, a trigger signal is transmitted through a signal layer. In this case, each of devices in the power off mode is set back into the normal mode.

FIG. 17 shows a cross-sectional structure of a 2D-DST board 620 of a signal communication apparatus in the fourth embodiment. The 2D-DST board 620 is provided with devices 630, power supply switch circuits 648 for selecting supply or shutoff of electrical power to the respective devices 630, a power supply layer 631 that supplies electrical power to the devices 630 and the power supply switch circuits 648, a ground layer 632 for grounding the devices 630, a signal layer 634 through which the transmission signal and trigger signal are transmitted from one of the devices 630 to another, and insulating layers 636 that electrically isolate the conductive layers (the power supply layer 631, ground layer 632, and signal layer 634) from each other. Each of the devices 630 includes a communicating part 638 for sending and receiving the transmission signal between itself and any adjacent ones thereto, and a processing part 640 that includes an antenna portion (not shown) configured to receive an image signal outputted from the capsule endoscope 100 and also carries out various kinds of processes in each of the devices 630. The signal layer 634 is connected to the power supply switch circuit 648. When the power supply switch circuit 648 detects a trigger signal 644 (a signal with a voltage equal to or higher than a predetermined voltage Vref), the device 630 is set back into the normal mode from the power off mode. In the case where the device 630 is set into the power off mode from the normal mode, a power off signal 650 is outputted from the device 630 to the power supply switch circuit 648, so that such a mode transition is made.

FIG. 18 is a detailed drawing around the power supply switch circuit 648 and the device 630 shown in FIG. 17. The power supply switch circuit 648 is provided with a comparator 668 for comparing the voltage of the transmission signal with the predetermined voltage Vref, a flip-flop (F. F.) 652, and a transistor 654.

In the fourth embodiment, the comparator 668 and the flip-flop 652 constitute a "switching means". The comparator 668 includes a first receiving terminal 670, a second receiving terminal 672, and an output terminal 674. The first receiving terminal 670 is a terminal to which the predetermined voltage Vref is inputted. The second receiving terminal 672 is a terminal to which the transmission signal including the trigger signal 644 is inputted. The output terminal 674 is a terminal configured to output a trigger detecting signal 676, which is generated based on signals that the first and second receiving terminals 670 and 672 have received. The comparator 668 detects the trigger signal 644 with a voltage that is equal to or higher than the predetermined voltage Vref included in the transmission signal, so as to generate the trigger detecting signal 676, which is then outputted to the flip-flop 652 via the output terminal 674.

The flip-flop 652 is provided with a first receiving terminal 662, a second receiving terminal 664, and an output terminal 666. The first receiving terminal 662 is connected with the output terminal 674. The first receiving terminal 662 is an input terminal to which the trigger detecting signal 676 is inputted. The second receiving terminal 664 is an input terminal for the power off signal 650 outputted from the device 630. The output terminal 666 is connected with the transistor 654.

The flip-flop 652 detects the trigger detecting signal 676 to output a signal for controlling the electrical connection or cutting between the power supply layer 631 and the device 630. When the trigger detecting signal 676 is inputted to the first receiving terminal 662 in the flip-flop 652, the output terminal 666 is connected to a power supply (not shown), and then outputs a voltage that is equal to or higher than a predetermined voltage. In contrast, when the power off signal 650 is inputted to the second receiving terminal 664, the electrical connection between the output terminal 666 and the power supply is cut off. Thereby, electrical power supply to the output terminal 666 is shut off, or is reduced to a level lower than the predetermined voltage.

The transistor 654 is provided with a base terminal 656, a collector terminal 658, and an emitter terminal 660. The base terminal 656 is connected with the output terminal 666 of the flip-flop 652. The collector terminal 658 is connected with the power supply layer 631. The emitter terminal 660 is connected with the device 630. The transistor 654 controls the electrical connection or cutting between the power supply layer 631 and the device 630. In the transistor 654, when the predetermined voltage or higher is inputted to the base 656, the collector terminal 658 and the emitter terminal 660 are electrically connected with one another.

In the above configuration, if the trigger detecting signal 676 is inputted to the first receiving terminal 662 while the device 630 is being operated in the power off mode, the flip-flop 652 will output the predetermined voltage or higher to the output terminal 666. Since the output terminal 666 is connected with the base terminal 656, the predetermined voltage or higher is applied to the base terminal 656. For this reason, the collector terminal 658 and the emitter terminal 660 are connected with one another, so that electrical power is supplied to the device 630 from the power supply layer 631.

In addition, if the power off signal 650 is inputted to the second receiving terminal 664 while the device 630 is being operated in the normal mode, the flip-flop 652 will output a voltage lower than the predetermined voltage to the output terminal 666. For this reason, the collector terminal 658 and the emitter terminal 660 are not electrically connected with one another, and consequently, electrical power supply to the device 630 from the power supply layer 631 is shut off. FIGS. 19A, 19B, 19C, and 19D show the relationship in time domain among the electrical power consumption level of the device 630, the power off signal 650, the trigger detecting signal 676, and the transmission signal.

FIG. 19A is a graph showing the change of the electrical power consumption level of the device 630 in time domain. The vertical axis of FIG. 19A represents the electrical power consumption level, and the horizontal axis thereof does time. FIG. 19B shows the timing of the power off signal 650 being generated. FIG. 19C shows the timing of the trigger detecting signal being generated. FIG. 19D shows the waveform of the transmission signal.

As shown in FIG. 19D, the transmission signal is a rectangular wave having substantially two flat voltage levels of H and L, which are lower than the predetermined voltage Vref. In contrast, the trigger signal 644 has a voltage level of T higher than Vref. The comparator 668 compares the transmission signal with the predetermined voltage Vref. Based on the comparison results, the comparator 668 detects a voltage, which is equal to or higher than Vref, included in the transmission signal as the trigger signal 644, then outputting the trigger detecting signal 676 to the flip-flop 652.

The device 630, which is being operated in the normal mode with an electrical power consumption level of P2, is set into the power off mode at a time of t7 with the power supply switch circuit 648 receiving the power off signal 650 from the device 630, for instance, after keeping such an operation without finding its own ID code in the transmission signal for a predetermined time period. Thereby, the electrical power consumption level becomes P0. Thereafter, at a time of t8, the trigger signal 644 is detected, so that the device 630 gets back in the normal mode with an electrical power consumption level of P2.

Next, a signal communication apparatus in a fifth embodiment will be described. In the fifth embodiment, each of devices that are being operated in the low electrical power consumption mode can be set back into the normal mode by a trigger signal transmitted through a power supply layer.

FIG. 20 shows a cross-sectional structure of a 2D-DST board 720 of a signal communication apparatus in the fifth embodiment. The 2D-DST board 720 is provided with devices 730, a power supply layer 731 for supplying electrical power to the devices 730, a ground layer for grounding the devices 730, a signal layer 734 for transmitting the transmission signal between one of the devices 730 and any adjacent ones thereto, and insulating layers 736 that electrically isolate the conductive layers (the power supply layer 731, signal layer 734, and ground layer 732) from each other.

Each of the devices 730 includes a communicating part 738, a processing part 740, a first power supply terminal 778, and a second power supply terminal 780. In addition, each of the devices 730 includes a system with the same configuration (not shown) as that of the power supply switch circuit 648 in the fourth embodiment (i.e., the comparator 668, the flip-flop 652, and the transistor 654). The communicating part 738 has a function for sending and receiving the transmission signal between one of the devices 730 and any adjacent ones thereto. The processing part 740 includes an antenna portion (not shown) configured to receive an image signal outputted from the capsule endoscope 100 and also carries out various kinds of processes in each of the devices 730. The first power supply terminal 778 is an alternative terminal for the collector terminal 658 in the fourth embodiment. The first power supply terminal 778 is configured to receive a voltage VCC1, which, for example, is generally provided from the control unit 220, from the power supply layer 731. The second power supply terminal 780 is an alternative terminal for the second receiving terminal 672 in the fourth embodiment. The second power supply terminal 780 is configured to receive, from the power supply layer 731, a trigger for setting the device 730 being operated in the low electrical power consumption mode back into the normal mode. The above trigger is a signal with a voltage VCC2 that is equal to or higher than the voltage VCC1 outputted from the control unit 220 or a power supply different from a usually used one. The comparator included in each of the devices 730 has a reference voltage input terminal, to which a voltage Vref (VCC1<Vref<VCC2) is inputted, in addition to the second power supply terminal 780. When a voltage equal to or higher than the voltage VCC2 is inputted to the second power supply terminal 780, the system, provided in the device 730, with the corresponding configuration to the power supply switch circuit 648 operates as described in the fourth embodiment. Thereby, the device 730 is set back into the normal mode from the low electrical power consumption mode. It is noted that only one of the first and second power supply terminals 778 and 780 may be connected with the power supply layer 731. In this case, the device 730 has to be configured to select the first power supply terminal 778 or the second power supply terminal 780 inside the device 730. In the fifth embodiment, the trigger signal, superimposed on the power supply voltage, is transmitted through the power supply layer 731, so that such a mode transition is accomplished. As a result, a trigger layer becomes unnecessary, which can make a 2D-DST board thinner, and can reduce the cost of the 2D-DST board.

Here, it is assumed that the device 730 is being operated in the low electrical power consumption mode. Therefore, functions excluding minimum necessary functions of the device 730 are being powered off. If a signal with a voltage of VCC2, in such a state, is transmitted through the power supply layer 731 to be inputted the device 730 via the second power supply terminal 780, the device 730 is set back into the normal mode from the low electrical power consumption mode. FIGS. 21A and 21B show the relationship in time domain between the electrical power consumption level of the device 730 and the voltage of the power supply layer 731.

FIG. 21A is a graph showing the change of the electrical power consumption level of the device 730 in time domain. The vertical axis of FIG. 21A represents the electrical power consumption level, and the horizontal axis thereof does time. FIG. 21B shows the voltage level of the power supply layer 731. For example, as shown in FIG. 21B, a voltage of VCC1 to be supplied to each of the devices 730, which is a driving voltage for driving each of the devices 730, is carried through the power supply layer 731 by the control unit 220. In this case, for instance, when the control unit 220 sends out a voltage equal to or higher than VCC2 as a trigger, which is then inputted to the second power supply terminal 780, the device 730 is set back into the normal mode from the low electrical power consumption mode.

As shown in FIG. 21A, the device 730, which is being operated in normal mode with an electrical power consumption level of P2, for instance, after keeping such an operation without finding its own ID code in the transmission signal for a predetermined time period, is set into the normal mode from the low electrical power consumption mode at a time of t9. Thereby, the electrical power consumption level becomes P1. Thereafter, at a time of t10, the device 730 is set back into the normal mode from the low electrical power consumption mode by detecting a voltage of VCC2. Thereby, the electrical power consumption level becomes P2.

Next, a signal communication apparatus in a sixth embodiment will be explained. In the sixth embodiment, each of devices being operated in the power off mode can be set back into the normal mode by a trigger signal transmitted through a power supply layer.

FIG. 22 shows a cross-sectional structure of a 2D-DST board 820 of a signal communication apparatus in the sixth embodiment. In the sixth embodiment, which corresponds to a variation of the fifth embodiment, a power supply switch circuit, which is incorporated in each of the devices in the fifth embodiment, is provided outside each of devices. The 2D-DST board 820 is provided with devices 830, power supply switch circuits 848 for selecting supply or shutoff of electrical power to the respective devices 830, a power supply layer 831 that supplies electrical power to the devices 830 and the power supply switch circuits 848, a ground layer 832 for grounding the devices 830, a signal layer 834 through which the transmission signal is transmitted from one of the devices 830 to another, and insulating layers 636 that electrically isolate the conductive layers (the power supply layer 831, signal layer 834, and ground layer 832) from each other. In addition, each of the devices 830 includes a communicating part 838 for sending and receiving the transmission signal between itself and any adjacent ones thereto, and a processing part 840 that includes an antenna portion (not shown) configured to receive an image signal outputted from the capsule endoscope 100 and also carries out various kinds of processes in each of the devices 830. In the case where the device 830 is set into the power off mode from the normal mode, a power off signal 850 is outputted from the device 830 to the power supply switch circuit 848, so that such a mode transition is made.

FIG. 23 is a detailed drawing around the power supply switch circuit 848 and the device 830 shown in FIG. 22. The power supply switch circuit 848 is provided with a comparator 868 for comparing the power supply voltage with a predetermined voltage Vref, a flip-flop (F. F.) 852, and a transistor 854.

In the sixth embodiment, the comparator 868 and the flip-flop 852 constitute a "switching means". A voltage of VCC1 to be supplied to each of the devices 830, which is a driving voltage for driving each of the devices 830, is carried through the power supply layer 831 by the control unit 220. In addition, the voltage of a signal for setting the device 830 back into the normal mode from the power off mode (i.e., a trigger signal) is a voltage of VCC2. The voltage VCC2, for example, is supplied from the control unit 220 or a power supply different from a usually used one. It is noted that the predetermined voltage Vref satisfies a following condition: VCC2>Vref>VCC1.

The comparator 868 is provided with a first receiving terminal 872, a second receiving terminal 880, and an output terminal 874. The first terminal 872 is a terminal to which the predetermined voltage Vref is inputted. The second receiving terminal 880 is a terminal to which the voltage of the power supply layer 831 is inputted. The output terminal is a terminal that outputs a trigger detecting signal 876 generated when a voltage received by the second receiving terminal 880 is higher than Vref.

The flip-flop 852 includes a first receiving terminal 862, a second receiving terminal 864, and an output terminal 866. The first receiving terminal 862 is a terminal that receives the trigger detecting signal 876. The second receiving terminal 864 is an input terminal for the power off signal 850 outputted from the device 830. The output terminal 866 is a terminal connected to the transistor 854.

In the flip-flop 852, when the trigger detecting signal 876 is inputted to the first receiving terminal 862, the output terminal 866 is connected to a power supply (not shown), and then output a predetermined voltage or higher. In contrast, when the power off signal 850 is inputted to the second receiving terminal 864, the electrical connection between the output terminal 866 and the power supply (not shown) is cut off. Thereby, electrical power supply to the output terminal 866 is shut off, or is reduced to a level lower than the predetermined voltage.

The transistor 854 is provided with a base terminal 856, a collector terminal 858, and an emitter terminal 860. The base terminal 856 is connected with the output terminal 866 of the flip-flop 852. The collector terminal 858 is connected with the power supply layer 831. The emitter terminal 860 is connected with the device 830. The transistor 854 controls the electrical connection or cutting between the power supply layer 831 and the device 830. In this transistor 854, when a predetermined voltage or more is inputted to the base terminal 856, the collector terminal 858 and the emitter terminal 860 are electrically connected with one another.

In the above configuration, if the trigger detecting signal 876 is inputted to the first receiving terminal 862 of the device 830 being operated in the power off mode, the flip-flop 852 will output the predetermined voltage or more to the output terminal 866. Since the output terminal 866 is connected with the base terminal 856, the predetermined voltage or more is applied to the base terminal 856. Consequently, the collector terminal 858 and the emitter terminal 860 are electrically connected with one another. Since the collector terminal 858 is connected with the power supply layer 831 via a receiving terminal 878, electrical power is supplied to the device 830 from the power supply layer 831.

It is noted that, in FIGS. 22 and 23, only one of the receiving terminal 878 and the second receiving terminal 880 of the power supply switch circuit 848 may be connected with the power supply layer 831. In this case, the power supply switch circuit 848 has to be configured such that electrical wiring, extending from an only receiving terminal connected with the power supply layer 831, diverges inside the power supply switch circuit 848.

Here, it is assumed that the device 830 is being operated in the normal mode. If the power off signal 850 is inputted to the second receiving terminal 864 of the flip-flop 852 in such a state, the flip-flop 852 will output less than the predetermined voltage to the output terminal 866. For this reason, the collector terminal 858 is not electrically connected with the emitter terminal 860, and consequently, electrical power supply to the device 830 from the power supply layer 831 is shut off. FIGS. 24A and 24B show the relationship in time domain between the electrical power consumption level of the device 830 and the voltage of the power supply layer 831.

FIG. 24A is a graph showing the change of the electrical power consumption level of the device 830. The vertical axis of FIG. 24A represents the electrical power consumption, and the horizontal axis does time. FIG. 24B is a graph showing the voltage of the power supply layer 831. For example, as shown in FIG. 24B, a voltage of VCC1 to be supplied to each of the devices 830, which is a driving voltage for driving each of the devices 830, is carried through the power supply layer 831 by the control unit 220. Here, for instance, if the control unit 220 sends out a voltage of VCC2 or more as a trigger, which is then inputted to the second receiving terminal 880 of the comparator 868, the device 830 will be set back into the normal mode from the power off mode.

As shown in FIG. 24A, the device 830, which is being operated in the normal mode with an electrical power consumption level of P2, for instance, after keeping such an operation without finding its own ID code in the transmission signal, is set into the power off mode at a time of t11. Thereby, the electrical power consumption level becomes P0. Thereafter, a voltage of VCC2 is detected at a time of t12, so that the device 830 is set back into the normal mode with an electrical power consumption of P2 from the power off mode.

Next, a signal communication apparatus in a seventh embodiment will be described. In the seventh embodiment, using the ID codes included in the transmission signal, each of devices being operated in the low electrical power consumption mode is set back into the normal mode.

FIG. 25A is a graph showing the change of the electrical power consumption level of the device 230 in time domain. The vertical axis of FIG. 25A represents the electrical power consumption level, and the horizontal axis thereof does time. FIG. 25B shows the waveform of the transmission signal in time domain.

As shown in FIG. 25A, each of the devices 230, which are not on the transmission channel, is being operated in the normal mode, and, for instance, after keeping such an operation without finding its own ID code for a predetermined time period, is set into the low electrical power consumption mode at a time of t13 (that is, all functions thereof except for the receiving function of the communicating part 38 are stopped). When each of the devices 230 in the low electrical power consumption mode finds its own ID code (or an ID code of a whole group including itself) in the received transmission signal, it is set back into the normal mode at a time of t14 in FIG. 25A. The ID codes included in the transmission signal, for example, may include an ID code of a source device sending the transmission signal, and/or ID codes of devices on a transmission channel.

In addition, in an alternative signal communication apparatus for that in the seventh embodiment, each of the devices 230 will be set back into the normal mode if its own ID code (or the ID code of the whole group including itself) is included in the transmission signal, and the ID code is identified as an ID code designated by a boot command for setting the devices back into the normal mode. Each of the devices 230 is not set back into the normal mode, when its own ID code is included in the transmission signal, yet the ID code is not identified as an ID code designated by the boot command.

Hereinbefore, the explanations of the first to the seventh embodiments have been made assuming that each of the devices is being operated in the low electrical power consumption mode or the power off mode. However, any of both modes may be applied in any embodiment.

The present disclosure relates to the subject matter contained in Japanese Patent Application No. P2004-351063, filed on Dec. 03, 2004, which is expressly incorporated herein by reference in its entirely.

What is claimed is:

1. An operation control method to be implemented by each of a plurality of communication devices two-dimensionally arranged on a two dimensional diffusive signal-transmission board, each of the plurality of communication devices being configured to communicate by transmitting a transmission signal carrying data to another of the plurality of communication devices using a two dimensional diffusive signal-transmission technology, the method comprising:

judging whether a communication device being operated in a normal mode satisfies a predetermined condition; and setting the communication device into one of a low electrical power consumption mode in which at least one function is decreased, and a power off mode in which electrical power supply to the communication device is shut off, when the communication device being operated in the normal mode satisfies the predetermined condition.

2. The operation control method according to claim 1, wherein the predetermined condition includes a condition where the communication device has not received the transmission signal for a predetermined time period.

3. The operation control method according to claim 1, wherein each of the plurality of communication devices is given its own ID to identify itself,
   wherein the transmission signal includes the IDs of the communication devices that are to be on a transmission channel, and
   wherein the predetermined condition includes a condition where the communication device has not received the transmission signal including its own ID for a predetermined time period.

4. The operation control method according to claim 1, wherein each of the plurality of communication devices is given its own ID to identify itself,
   wherein the transmission signal includes a sleep command designating the IDs to be set into one of the low electrical power consumption mode and the power off mode, and
   wherein the predetermined condition includes a condition where the ID of the device corresponds to one of the IDs designated by the sleep command included in the transmission signal received by the device.

5. The operation control method according to claim 1,
   wherein each of the plurality of communication devices is given its own ID to identify itself,
   wherein the transmission signal includes the IDs of the communication devices that are to be on a transmission channel, and a sleep command designating the IDs to be set into one of the low electrical power consumption mode and the power off mode, and
   wherein the predetermined condition includes at least one of a first condition where the communication device has not received the transmission signal for a predetermined time period, a second condition where the communication device has not received the transmission signal including its own ID for a predetermined time period, and a third condition where the ID of the device corresponds to one of the IDs designated by the sleep command included in the transmission signal received by the device.

6. The operation control method according to claim 1,
   wherein the communication device is set back into the normal mode, when it receives an external trigger while being operated in one of the low electrical power consumption mode and the power off mode.

7. A signal communication apparatus, comprising:
   a plurality of communication devices two-dimensionally arranged on a board, each of the plurality of communication devices being configured to communicate using a two dimensional diffusive signal-transmission technology; and
   a control unit configured to control the whole of the signal communication apparatus,
   wherein the board comprises:
   a power supply layer configured to supply electrical power to each of the plurality of communication devices;
   a ground layer configured to ground each of the plurality of communication devices;
   a signal layer configured such that a transmission signal is transmitted among the plurality of communication devices; and
   a plurality of insulating layers configured to electrically isolate the power supply layer, the ground layer, and the signal layer from each other.

8. The signal communication apparatus according to claim 7,
   wherein each of the plurality of communication devices includes an antenna configured to receive a signal outputted from an external sensor.

9. The signal communication apparatus according to claim 7,
   wherein each of the plurality of communication devices includes a trigger detecting system configured to detect an external trigger.

10. The signal communication apparatus according to claim 9,
    wherein the board further includes a trigger layer configured such that the trigger detecting system detects the external trigger transmitted therethrough.

11. The signal communication apparatus according to claim 9,
    wherein the trigger detecting system is configured to detect the external trigger transmitted through one of the power supply layer and the signal layer.

12. The signal communication apparatus according to claim 9,
wherein the trigger detecting system includes a switching system configured to select one of electrical connection and cutting between the power supply layer and the communication device.

13. The signal communication apparatus according to claim 9,
wherein the trigger detecting system includes a comparing system configured to compare a signal including the external trigger with a reference signal.

14. The signal communication apparatus according to claim 9,
wherein each of the plurality of communication devices is configured to be set into one of a low electrical power consumption mode in which at least a part of functions thereof is brought down, and a power off mode in which electrical power supply thereto is shut off, when it satisfies a predetermined condition while being operated in a normal mode.

15. The signal communication apparatus according to claim 14,
wherein the predetermined condition includes a condition where the communication device has not received the transmission signal for a predetermined time period.

16. The signal communication apparatus according to claim 14,
wherein each of the plurality of communication devices is given its own ID to identify itself,
wherein the transmission signal includes the IDs of the communication devices that are to be on a transmission channel, and
wherein the predetermined condition includes a condition where the communication device has not received the transmission signal including its own ID for a predetermined time period.

17. The signal communication apparatus according to claim 14,
wherein each of the plurality of communication devices is given its own ID to identify itself,
wherein the transmission signal includes a sleep command designating the IDs to be set into one of the low electrical power consumption mode and the power off mode, and
wherein the predetermined condition includes a condition where the ID of the device corresponds to one of the IDs designated by the sleep command included in the transmission signal received by the device.

18. The signal communication apparatus according to claim 14,
wherein each of the plurality of communication devices is given its own ID to identify itself,
wherein the transmission signal includes the IDs of the communication devices that are to be on a transmission channel, and a sleep command designating the IDs to be set into one of the low electrical power consumption mode and the power off mode, and
wherein the predetermined condition includes at least one of a first condition where the communication device has not received the transmission signal for a predetermined time period, a second condition where the communication device has not received the transmission signal including its own ID for a predetermined time period, and a third condition where the ID of the device corresponds to one of the IDs designated by the sleep command included in the transmission signal received by the device.

19. The signal communication apparatus according to claim 14,
wherein the communication device operated in one of the low electrical power consumption mode and the power off mode is set back into the normal mode, when it receives an external trigger.

20. Clothing, comprising a signal communication apparatus, which comprises:
a plurality of communication devices two-dimensionally arranged on a board, each of the plurality of communication devices being configured to communicate using a two dimensional diffusive signal-transmission technology; and
a control unit configured to control the whole of the signal communication apparatus,
wherein the board comprises:
a power supply layer configured to supply electrical power to each of the plurality of communication devices;
a ground layer configured to ground each of the plurality of communication devices;
a signal layer configured such that a transmission signal is transmitted among the plurality of communication devices; and
a plurality of insulating layers configured to electrically isolate the power supply layer, the ground layer, and the signal layer from each other,
wherein each of the plurality of communication devices comprises:
an antenna configured to receive a signal outputted from an external sensor; and
a trigger detecting system configured to detect an external trigger, and
wherein each of the plurality of communication devices is configured to be set into one of a low electrical power consumption mode in which at least one function is lowered, and a power off mode in which electrical power supply thereto is shut off, when it satisfies a predetermined condition while being operated in a normal mode, and
wherein each of the plurality of communication devices is configured to be set back into the normal mode, when it receives the external trigger while being operated in one of the low electrical power consumption mode and the power off mode.

* * * * *